US012611137B2

(12) United States Patent
Baldwin et al.

(10) Patent No.: US 12,611,137 B2
(45) Date of Patent: Apr. 28, 2026

(54) LYMPHATIC DIAGNOSTIC DEVICE

(71) Applicant: Koya Medical, Inc., Oakland, CA (US)

(72) Inventors: Jarren Baldwin, Oakland, CA (US);
John C. Pamplin, Oakland, CA (US);
Jay Zuerndorfer, Oakland, CA (US);
Jackson C. Wilson, Evanston, IL (US);
Michael C. Garrett, Wilmette, IL (US);
Frank E. Garrett, Barrington, IL (US);
Anand Doraiswamy, Oakland, CA
(US); Bilal Filali, Coquitlam (CA)

(73) Assignee: Koya Medical, Inc., Dallas, TX (US)

( * ) Notice: Subject to any disclaimer, the term of this
patent is extended or adjusted under 35
U.S.C. 154(b) by 627 days.

(21) Appl. No.: 17/848,289

(22) Filed: Jun. 23, 2022

(65) Prior Publication Data

US 2022/0409123 A1 Dec. 29, 2022

Related U.S. Application Data

(60) Provisional application No. 63/215,396, filed on Jun.
25, 2021.

(51) Int. Cl.
| | |
|---|---|
| *A61B 5/00* | (2006.01) |
| *A61B 5/01* | (2006.01) |
| *A61B 5/0531* | (2021.01) |
| *A61B 90/00* | (2016.01) |

(52) U.S. Cl.
CPC ............ *A61B 5/418* (2013.01); *A61B 5/0008*
(2013.01); *A61B 5/01* (2013.01); *A61B 5/0531*
(2013.01); *A61B 5/442* (2013.01); *A61B*
*5/4878* (2013.01); *A61B 5/684* (2013.01);
*A61B 5/7246* (2013.01); *A61B 5/742*
(2013.01);
(Continued)

(58) Field of Classification Search
CPC ......... A61B 5/418; A61B 5/0008; A61B 5/01;
A61B 5/0531; A61B 5/442; A61B
5/4878; A61B 5/684; A61B 5/7246; A61B
5/742; A61B 2090/065; A61B 2503/40;
A61B 2562/0271; A61N 1/0456; A61N
1/3603
See application file for complete search history.

(56) References Cited

U.S. PATENT DOCUMENTS

| | | | |
|---|---|---|---|
| 4,018,064 A | 4/1977 | Doslik | |
| 4,527,402 A | 7/1985 | Swallow et al. | |
| | (Continued) | | |

FOREIGN PATENT DOCUMENTS

| | | |
|---|---|---|
| CN | 101098670 B | 7/2011 |
| CN | 103941909 A | 7/2014 |
| | (Continued) | |

OTHER PUBLICATIONS

International Search Report and Written Opinion in Application No.
PCT/US2022/073120, mailed on Sep. 9, 2022, in 16 pages.

*Primary Examiner* — Carl H Layno
*Assistant Examiner* — Anh-Khoa N Dinh
(74) *Attorney, Agent, or Firm* — Knobbe, Martens, Olson
& Bear, LLP

(57) ABSTRACT

Diagnostic devices can be used for diagnosing lymphedema.
The diagnostic devices may include an array of sensors,
which can at least include a durometer, temperature sensor,
and dielectric sensor, to measure parameters of tissue. The
measurements may be used to generate a tissue health score
to diagnose lymphedema and monitor tissue heath.

10 Claims, 19 Drawing Sheets

(52) U.S. Cl.

CPC ..... *A61B 2090/065* (2016.02); *A61B 2503/40* (2013.01); *A61B 2562/0271* (2013.01)

(56) References Cited

U.S. PATENT DOCUMENTS

| | | | |
|---|---|---|---|
| 4,860,753 A * | 8/1989 | Amerena | A61B 5/442 |
| | | | 324/690 |
| 5,001,436 A * | 3/1991 | Scot | A61B 5/442 |
| | | | 324/692 |
| 5,144,753 A * | 9/1992 | Murphy | G01B 5/18 |
| | | | 33/514 |
| 5,787,732 A | 8/1998 | Perron et al. | |
| 5,904,658 A * | 5/1999 | Niederauer | G01N 33/4833 |
| | | | 600/587 |
| 5,996,205 A | 12/1999 | Mashiko et al. | |
| 5,997,465 A | 12/1999 | Savage et al. | |
| 6,123,681 A | 9/2000 | Brown, III | |
| 6,190,344 B1 | 2/2001 | Bobroff | |
| 6,509,094 B1 | 1/2003 | Shah et al. | |
| 6,656,141 B1 | 12/2003 | Reid | |
| 7,135,007 B2 | 11/2006 | Scott et al. | |
| 7,857,777 B2 | 12/2010 | Larson et al. | |
| 7,868,221 B2 | 1/2011 | Munch-Fals et al. | |
| 7,896,825 B2 | 3/2011 | Atkinson et al. | |
| 8,359,716 B2 | 1/2013 | Fiedler | |
| 8,517,963 B2 | 8/2013 | Larson et al. | |
| 8,523,794 B2 | 9/2013 | Iker et al. | |
| 8,764,689 B2 | 7/2014 | Toth | |
| 8,801,643 B2 | 8/2014 | Deshpande et al. | |
| 9,027,408 B2 | 5/2015 | Toth | |
| 9,161,878 B1 | 10/2015 | Pamplin et al. | |
| 9,248,074 B2 | 2/2016 | Toth | |
| 9,271,676 B2 | 3/2016 | Alanen et al. | |
| 9,271,890 B1 | 3/2016 | Pamplin et al. | |
| 9,326,911 B2 | 5/2016 | Wyatt et al. | |
| 9,421,142 B2 | 8/2016 | Malhi et al. | |
| 9,463,821 B1 | 10/2016 | Critchley et al. | |
| 9,516,923 B2 | 12/2016 | Capra et al. | |
| 9,555,935 B2 | 1/2017 | Fiedler | |
| 9,572,410 B2 | 2/2017 | Fiedler | |
| 9,677,581 B2 | 6/2017 | Tucholke et al. | |
| 9,700,102 B2 | 7/2017 | McCleary et al. | |
| 9,907,367 B2 | 3/2018 | Paik et al. | |
| 9,936,772 B2 | 4/2018 | Paik | |
| 10,071,012 B2 | 9/2018 | Larson et al. | |
| 10,085,521 B2 | 10/2018 | Chen et al. | |
| 10,098,422 B2 | 10/2018 | Fiedler et al. | |
| 10,111,500 B2 | 10/2018 | Lambert | |
| 10,143,270 B2 | 12/2018 | Fiedler et al. | |
| 10,188,152 B2 | 1/2019 | Stasey et al. | |
| 10,206,461 B1 | 2/2019 | Swetish | |
| 10,285,902 B2 | 5/2019 | Pamplin et al. | |
| 10,307,074 B2 | 6/2019 | Ward | |
| 10,426,202 B2 | 10/2019 | Wyatt et al. | |
| 10,441,491 B2 | 10/2019 | Wyatt et al. | |
| 10,617,593 B2 | 4/2020 | Wyatt et al. | |
| 10,668,305 B2 | 6/2020 | Cheatham, III et al. | |
| 10,688,007 B2 | 6/2020 | Wyatt et al. | |
| 10,743,621 B2 | 8/2020 | Wyatt et al. | |
| 10,791,992 B1 | 10/2020 | Desai et al. | |
| 10,893,968 B2 | 1/2021 | Wetzel et al. | |
| 11,406,561 B2 | 8/2022 | Pamplin et al. | |
| 11,471,368 B2 | 10/2022 | Doraiswamy et al. | |
| 11,583,038 B2 | 2/2023 | Doraiswamy et al. | |
| 11,672,729 B2 | 6/2023 | Doraiswamy et al. | |
| 11,707,405 B2 | 7/2023 | Pamplin et al. | |
| 11,903,895 B2 | 2/2024 | Pamplin et al. | |
| 12,156,571 B2 | 12/2024 | Doraiswamy et al. | |
| 2002/0156401 A1 | 10/2002 | Sherman et al. | |
| 2003/0005558 A1 | 1/2003 | Wong | |
| 2003/0045821 A1 | 3/2003 | Iker | |
| 2003/0187366 A1 | 10/2003 | Hashimshony | |
| 2005/0043657 A1 | 2/2005 | Couvillon, Jr. | |
| 2005/0203435 A1 * | 9/2005 | Nakada | A61B 5/0537 |
| | | | 600/547 |

| | | | |
|---|---|---|---|
| 2006/0162332 A1 | 7/2006 | Klaffenbach et al. | |
| 2008/0057526 A1 | 3/2008 | Caduff et al. | |
| 2008/0319359 A1 | 12/2008 | Moomiaie-Qajar et al. | |
| 2009/0076732 A1 * | 3/2009 | Sprigle | A61B 5/442 |
| | | | 702/19 |
| 2010/0056966 A1 | 3/2010 | Toth | |
| 2010/0056973 A1 | 3/2010 | Farrow et al. | |
| 2010/0234779 A1 | 9/2010 | Asvadi et al. | |
| 2010/0262135 A1 | 10/2010 | Berube | |
| 2010/0312160 A1 | 12/2010 | Creighton et al. | |
| 2011/0138583 A1 | 6/2011 | Fielder | |
| 2011/0139835 A1 | 6/2011 | Fikes | |
| 2011/0189444 A1 | 8/2011 | Beers | |
| 2012/0016210 A1 | 1/2012 | Kim et al. | |
| 2012/0065561 A1 | 3/2012 | Ballas et al. | |
| 2012/0101417 A1 | 4/2012 | Joseph | |
| 2012/0232447 A1 | 9/2012 | Gordon et al. | |
| 2013/0030335 A1 | 1/2013 | Norton | |
| 2013/0072837 A1 | 3/2013 | Rousso et al. | |
| 2013/0245388 A1 * | 9/2013 | Rafferty | A61B 8/4416 |
| | | | 600/307 |
| 2013/0267995 A1 | 10/2013 | Voss et al. | |
| 2013/0303957 A1 | 11/2013 | Bauerfeind | |
| 2014/0081187 A1 | 3/2014 | Wyatt et al. | |
| 2014/0277103 A1 | 9/2014 | Esposito | |
| 2015/0025426 A1 | 1/2015 | Larson et al. | |
| 2015/0065930 A1 | 3/2015 | Wyatt et al. | |
| 2015/0073318 A1 | 3/2015 | Holschuh et al. | |
| 2015/0073319 A1 | 3/2015 | Holschuh et al. | |
| 2015/0133836 A1 | 5/2015 | Pollock | |
| 2016/0022528 A1 | 1/2016 | Wyatt et al. | |
| 2016/0058644 A1 | 3/2016 | Cheatham, III et al. | |
| 2016/0074234 A1 | 3/2016 | Abichandani et al. | |
| 2016/0120733 A1 | 5/2016 | Ishikawa et al. | |
| 2016/0193100 A1 | 7/2016 | Toth | |
| 2016/0220808 A1 | 8/2016 | Hyde et al. | |
| 2016/0331620 A1 | 11/2016 | Kazanchyan et al. | |
| 2016/0374886 A1 | 12/2016 | Wyatt et al. | |
| 2017/0196347 A1 | 7/2017 | Sawhney et al. | |
| 2017/0246073 A1 | 8/2017 | Van-De-Velde | |
| 2017/0252252 A1 | 9/2017 | Wyatt et al. | |
| 2017/0304136 A1 | 10/2017 | Holschuh et al. | |
| 2017/0304139 A1 | 10/2017 | Ross | |
| 2017/0312161 A1 | 11/2017 | Johnson et al. | |
| 2018/0055009 A1 | 3/2018 | Wyatt et al. | |
| 2018/0125173 A1 | 5/2018 | Lambert | |
| 2018/0177677 A1 | 6/2018 | Pamplin et al. | |
| 2018/0192745 A1 | 7/2018 | McDaniel | |
| 2018/0214616 A1 | 8/2018 | Muschalek et al. | |
| 2018/0242655 A1 | 8/2018 | Holschuh et al. | |
| 2018/0368533 A1 | 12/2018 | Chan | |
| 2019/0274372 A1 | 9/2019 | Rizzo et al. | |
| 2020/0000676 A1 | 1/2020 | Pamplin et al. | |
| 2020/0000677 A1 | 1/2020 | Pamplin et al. | |
| 2020/0154804 A1 | 5/2020 | Huang | |
| 2020/0297569 A1 | 9/2020 | Angelo et al. | |
| 2020/0316365 A1 | 10/2020 | Hyde et al. | |
| 2021/0386614 A1 | 12/2021 | Doraiswamy et al. | |
| 2022/0022606 A1 | 1/2022 | Doraiswamy et al. | |
| 2022/0409437 A1 | 12/2022 | Pamplin et al. | |
| 2023/0117892 A1 | 4/2023 | Doraiswamy et al. | |
| 2023/0248579 A1 | 8/2023 | Evans et al. | |
| 2023/0270213 A1 | 8/2023 | Doraiswamy et al. | |
| 2024/0261177 A1 | 8/2024 | Pamplin et al. | |

FOREIGN PATENT DOCUMENTS

| | | | |
|---|---|---|---|
| CN | 105082129 A | 11/2015 | |
| CN | 105804960 | 7/2016 | |
| FR | 3123202 | 12/2022 | |
| KR | 10-1569850 | 11/2015 | |
| WO | WO 2013/025481 | 2/2013 | |
| WO | WO 2013/149985 | 10/2013 | |
| WO | WO 2014/172248 | 10/2014 | |
| WO | WO 2016/048827 | 3/2016 | |
| WO | WO 2016/077150 | 5/2016 | |
| WO | WO 2017/027145 | 2/2017 | |
| WO | WO 2018/013188 | 1/2018 | |
| WO | WO 2018/150372 | 8/2018 | |

(56)                         References Cited

FOREIGN PATENT DOCUMENTS

| WO | WO 2020/144437 | 7/2020 |
| WO | WO 2021/150619 | 7/2021 |
| WO | WO 2021/252770 | 12/2021 |
| WO | WO 2022/020370 | 1/2022 |
| WO | WO 2022/272285 | 12/2022 |
| WO | WO 2022/272287 | 12/2022 |
| WO | WO 2023/154707 | 8/2023 |

* cited by examiner

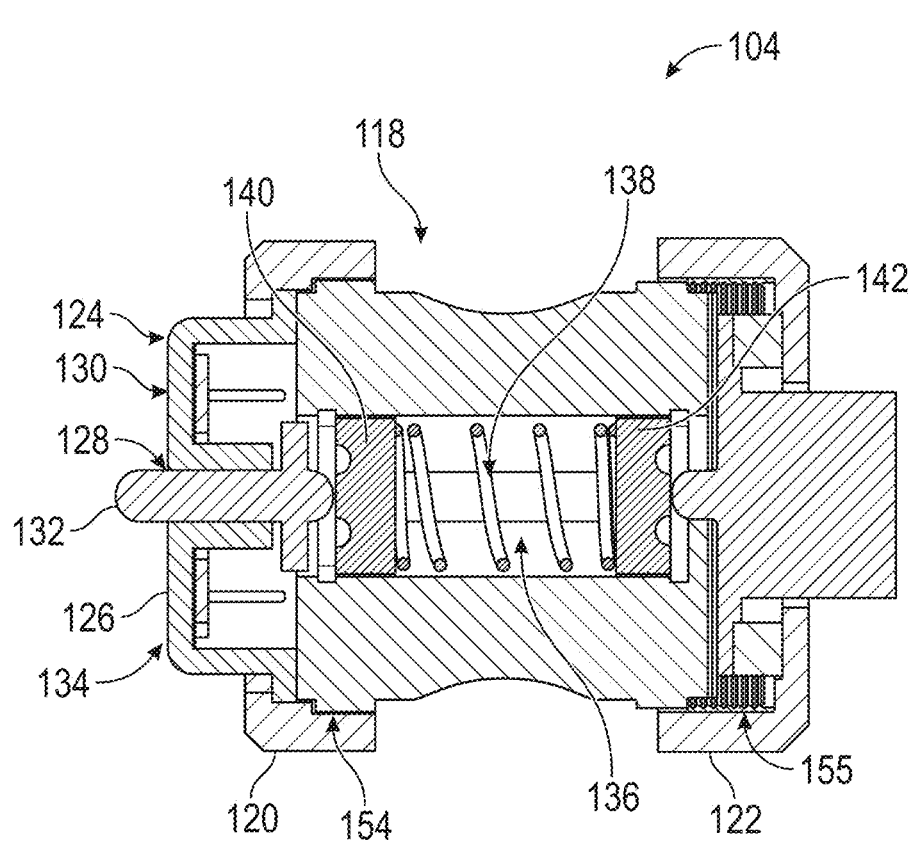
FIG. 4
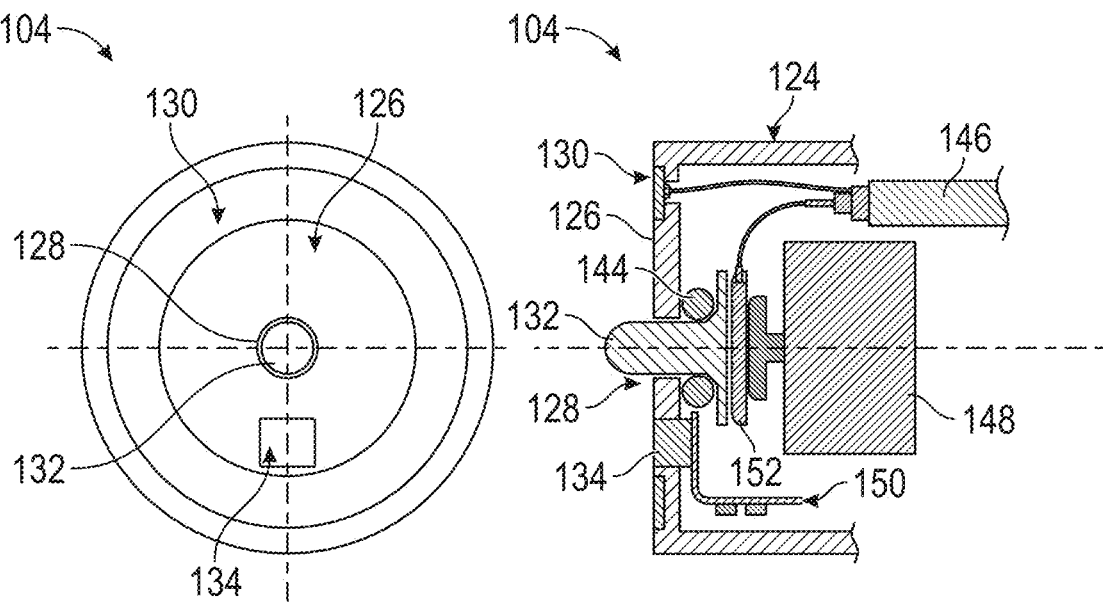
FIG. 5A                    FIG. 5B

Time (Days)

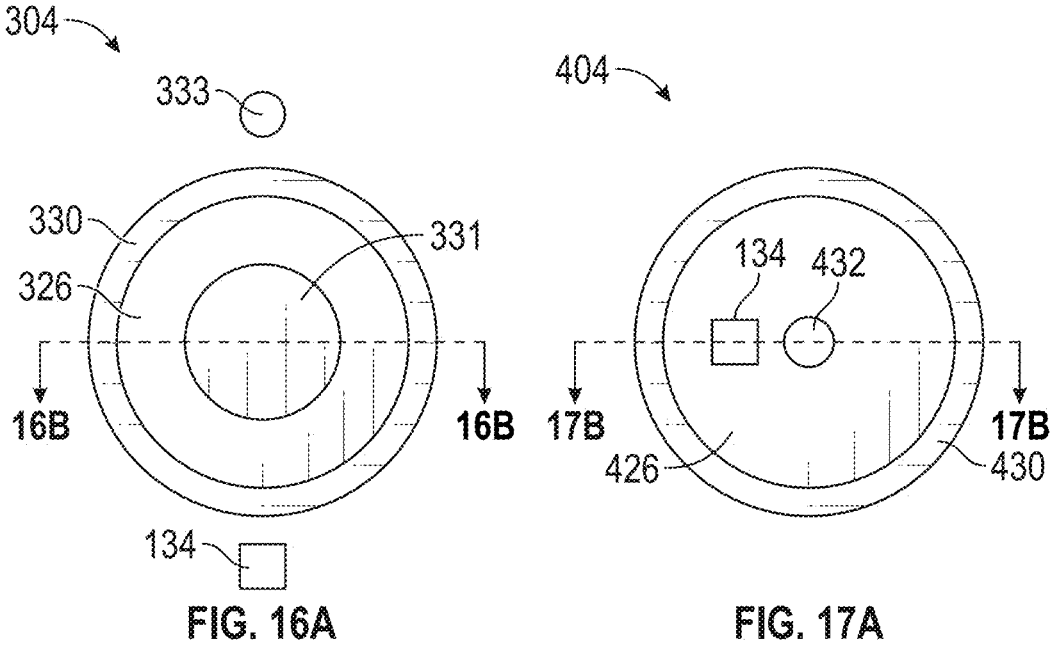
FIG. 16A                    FIG. 17A
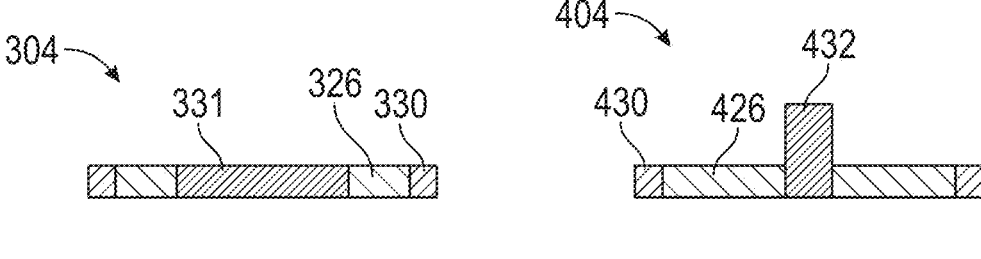
FIG. 16B                    FIG. 17B

LYMPHATIC DIAGNOSTIC DEVICE

CROSS REFERENCE

This application claims the priority benefit of U.S. Provisional Application No. 63/215,396, filed Jun. 25, 2021, which is hereby incorporated by reference in its entirety. All applications for which a foreign or domestic priority is identified in the Application Data Sheet as filed with the present application are hereby incorporated by reference under 37 CFR 1.57.

FIELD

This disclosure relates to diagnostic devices, specifically to lymphatic diagnostic devices for diagnosing lymphedema.

BACKGROUND

Lymphedema is a medical condition in which excess fluid, such as lymph fluid, collects in the body. In some instances, this excess fluid may collect in a specific area of the body, such as a limb, and cause swelling (i.e., edema). Left untreated, numerous additional symptoms may occur such as infections, fatigue, restricted range of motion, hardening of the skin/tissue, etc.

SUMMARY

Lymphedema and other skin conditions can be difficult to diagnose. Often, a skilled practitioner, even with years of training, experience, and education, can have difficulty identifying the severity of skin and/or lymphatic deterioration. Disclosed herein are diagnostic devices, systems, and related components that can be used to diagnose lymphedema and/or other skin conditions. The diagnostic devices can provide a real time metric to aid in diagnosis. The diagnostic device can measure one or more parameters, such as temperature, percent water content, bioimpedance, hardness or elasticity, oxygen content, pulse rate, electromagnetic reflection in the visual and non-visual spectrum, and/or others. The data captured for the one or more parameters can be cleaned or filtered. The cleaned or filtered data can be used as inputs for an algorithm to generate a tissue health score, which can be a metric used by patients and/or clinicians to aid in diagnosis and treatment. Incorporating multiple parameters to generate a tissue health score can provide for a more robust indication of the health of underlying tissue for a variety of conditions including, but not limited to, lymphedema, edema, circulatory insufficiency, tissue health, ulceration, cellulitis, fibrosis, venous insufficiencies, and/or others.

In some variants, a diagnostic device for measuring two or more parameters is disclosed herein. The diagnostic device can include one or more sensors that can measure the two or more parameters. The diagnostic device can include a display that can display the measured two or more parameters and/or a tissue health score.

In some variants, the two or more parameters can include temperature, percent water content, bioimpedance, and/or hardness or elasticity.

In some variants, the two or more parameters can include oxygen content, pulse rate, and/or electromagnetic reflection in the visual and/or nonvisual spectrum.

In some variants, temperature can be measured at skin of the user.

In some variants, temperature can be measured subcutaneous.

In some variants, the two or more sensors can measure the two or more parameters simultaneously.

In some variants, the two or more sensors can measure the two or more parameters in succession.

In some variants, the two or more sensors can measure the two or more parameters at approximately the same point on a body of a user.

In some variants, the two or more sensors can measure the two or more parameters at multiple points on a body of a user.

In some variants, the two or more parameters can be used to generate the tissue score.

In some variants, the measurements of the two or more parameters can be taken anywhere on a human or animal.

In some variants, the measurements of the two or more parameters can be taken at a location on a human or animal body and associated with a map to facilitate tracking measurements at the same location over multiple measurements.

In some variants, the measurements of the two or more parameters can be tracked over time.

In some variants, the measurements of the two or more parameters can be stored on the diagnostic device.

In some variants, the diagnostic device can be in communication with a remote device. The diagnostic device can communicate the measurements of the two or more parameters and/or tissue health score to the remote device.

In some variants, the display of the diagnostic device can prompt the user to measure the two or more parameters at a location on a human or animal.

In some variants, a display of a remote device in communication with the diagnostic device can prompt the user to measure the two or more parameters at a location on a human or animal.

In some variants, the diagnostic device can be used by a trained or untrained user in a hospital, clinic, or home environment.

In some variants, the tissue health score can be generated by way of an algorithm that uses the measurements for the two or more parameters as inputs.

In some variants, measurement data for the two or more parameters can be cleaned.

In some variants, the two or more parameters can be weighted equally by the algorithm.

In some variants, measurement data for the two or more parameters can be weighted unequally by the algorithm.

In some variants, measurements of the two or more parameters and/or tissue health score can be used to determine a tissue health trend, disease diagnosis, and/or recommended treatment.

In some variants, the display can output information regarding tissue health trend, disease diagnosis, and/or recommended treatment.

In some variants, the tissue health score or derivatives thereof can be used to guide treatment for one or more diseases.

In some variants, the one or more diseases can include edema, ulceration, cellulitis, fibrosis, and/or venous insufficiencies.

In some variants, the tissue health score can be generated from a comparison of the measurements for the two or more parameters and/or tissue health score with measurement data for the two or more parameters and/or tissue health score associated with healthy tissue and/or unhealthy tissue.

In some variants, the diagnostic device can be used to measure edema, lymphedema, circulatory insufficiency, and tissue health.

In some variants, the diagnostic device can automatically take measurements for the two or more parameters when pressed against skin or manually take measurements upon receiving user input.

In some variants, the two or more parameters can include temperature. Temperature can be measured with thermocouples, a resistance temperature detector, thermistors, a semiconductor based integrated circuit, and/or infrared thermometer.

In some variants, the two or more parameters can include percent water content/bioimpedance. Percent water content/ bioimpedance can be measured with multiple-frequency bioimpedance analysis (MFBIA), spectroscopic imaging, derivative spectroscopy visible, infrared, and ultraviolet spectrum, and/or an open-ended coaxial probe.

In some variants, the two or more parameters can include hardness.

Hardness can be measured with a durometer, single or multiple force transducers, strain transducer, pressure transducer, and/or suction with optical movement sensor.

In some variants, the two or more parameters can include oxygen content. Oxygen content can be measured with spectroscopic imaging, derivative spectroscopy visible, infrared, and/or ultraviolet spectrum.

In some variants, the two or more parameters can include pulse rat. Pulse rate can be measured with spectroscopic imaging, derivative spectroscopy visible, infrared, and ultraviolet spectrum, and/or near-field coherent sensing.

In some variants, two or more parameters can include electromagnetic reflection. Electromagnetic reflection can be measured with a digital camera sensor and/or photodiode.

In some variants, the diagnostic device can include a head assembly that can have a durometer probe, temperature sensor, dielectric conductor, and ground conductor. In some variants, the diagnostic device can include a head assembly that can have a durometer probe, temperature sensor, dielectric conductor, and/or ground conductor.

In some variants, the ground conductor can include a ring shape and the dielectric conductor can be centered within the ring shape.

In some variants, the durometer probe may be disposed within a periphery of the ground conductor.

In some variants, the temperature sensor may be disposed within a periphery of the ground conductor.

In some variants, the durometer probe may be disposed outside a periphery of the ground conductor.

In some variants, the temperature sensor may be disposed outside a periphery of the ground conductor.

In some variants, the diagnostic device can include an electrical insulator that may be disposed between the dielectric conductor and the ground conductor.

In some variants, the diagnostic device can include a head assembly that can include a probe, ground conductor, and a temperature sensor. The probe can be used to take dielectric measurements and measure hardness. In some variants, the diagnostic device can include a head assembly that can include a probe, ground conductor, and/or a temperature sensor.

In some variants, the diagnostic device can include a head assembly that can include a probe, ground conductor, and a temperature sensor. The probe can be used to take dielectric measurements and measure elasticity.

In some variants, the ground conductor can include a ring shape.

In some variants, the probe may be disposed within a periphery of the ground conductor.

In some variants, the probe may be positioned coaxially with the ground conductor.

In some variants, the head assembly can include a force transducer body, a force transducer tip, and a spring disposed between the force transducer body and the force transducer tip. The probe may be pushed by tissue to translate the force transducer tip toward the force transducer body to measure hardness.

In some variants, the head assembly can include a force transducer body, a force transducer tip, and a spring disposed between the force transducer body and the force transducer tip. The probe may be pushed by tissue to translate the force transducer tip toward the force transducer body to measure elasticity of the tissue.

In some variants, the diagnostic device may include an insulator that can be disposed between the probe and the ground conductor.

In some variants, the diagnostic device may include an insulator that may be disposed between the probe and the ground conductor. The insulator may be offset from a leading edge of the ground conductor such that an air gap is disposed between the probe and the ground conductor.

In some variants, a diagnostic device for measuring two or more parameters of tissue is disclosed herein. The diagnostic device may include one or more sensors that can measure the two or more parameters to generate a tissue health score for the tissue.

In some variants, a diagnostic device for measuring a hardness and a bioimpedance of tissue is disclosed herein. The diagnostic device may include a ground conductor. The diagnostic device may include a probe that can take dielectric measurements to measure the bioimpedance of tissue and to measure the hardness of tissue.

In some variants, the dielectric and hardness measurements can be used to generate a tissue health score for the tissue.

In some variants, the diagnostic device may include a temperature sensor configured to measure a temperature of tissue.

In some variants, the dielectric, hardness, and temperature measurements are used to generate a tissue health score for the tissue.

In some variants, the diagnostic device may include an insulator that can be disposed between the probe and the ground conductor.

In some variants, the probe may be disposed within a periphery of the ground conductor.

In some variants, the ground conductor can include a ring shape.

In some variants, the diagnostic device may include a force transducer body, a force transducer tip, and a spring disposed between the force transducer body and the force transducer tip. The probe may be pushed by the tissue to translate the force transducer tip toward the force transducer body to measure hardness.

In some variants, the diagnostic device can include an insulator that may be disposed between the probe and the ground conductor. The insulator may be offset from a leading edge of the ground conductor such that an air gap is disposed between the probe and the ground conductor.

In some variants, the probe may be used to take dielectric measurements to measure the bioimpedance of tissue and to measure the hardness of tissue simultaneously.

In some variants, the diagnostic device may include a transducer. The probe may apply a force to the transducer to measure the hardness of the tissue.

In some variants, the diagnostic device may prompt a user to take measurements at a location on a body of the user.

In some variants, a computing device in communication with the diagnostic device may prompt a user to take measurements at a location on a body of the user.

Neither the preceding summary nor the following detailed description purports to limit or define the scope of protection. The scope of protection is defined by the claims. Furthermore, reference is made herein to diagnosing lymphedema. However, one of skill in the art will understand, after reviewing the entirety of this disclosure, that the diagnostic devices, methods, systems, components, etc. described herein may be used for other purposes besides diagnosing and/or monitoring lymphedema. For example, the diagnostic devices, methods, systems, components, etc. described herein can be used to diagnose and/or monitor edema, lymphedema, circulatory insufficiency, tissue health. Furthermore, the diagnostic devices, methods, systems, components, etc. may be used for both humans and animals.

BRIEF DESCRIPTION OF THE DRAWINGS

The abovementioned and other features of the embodiments disclosed herein are described below with reference to the drawings of the embodiments. The illustrated embodiments are intended to illustrate, but not to limit, the scope of protection. Various features of the different disclosed embodiments can be combined to form further embodiments, which are part of this disclosure.

FIG. 4 illustrates a head assembly for a diagnostic device.

FIG. 5A illustrates a contact surface of a nose of the head assembly.

FIG. 5B illustrates a section view of the nose of the head assembly of FIG. 5A.

FIG. 16A illustrates another head assembly for a diagnostic device.

FIG. 16B illustrates a side cross-section view of the head assembly of FIG. 16A.

FIG. 17A illustrates another head assembly for a diagnostic device.

FIG. 17B illustrates a side cross-section view of the head assembly of FIG. 17A.

DETAILED DESCRIPTION

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below. Furthermore, this disclosure describes many embodiments in reference to treating lymphedema, but as described herein, any embodiment and modifications or equivalents thereof should not be limited to treating lymphedema.

Figure 1:
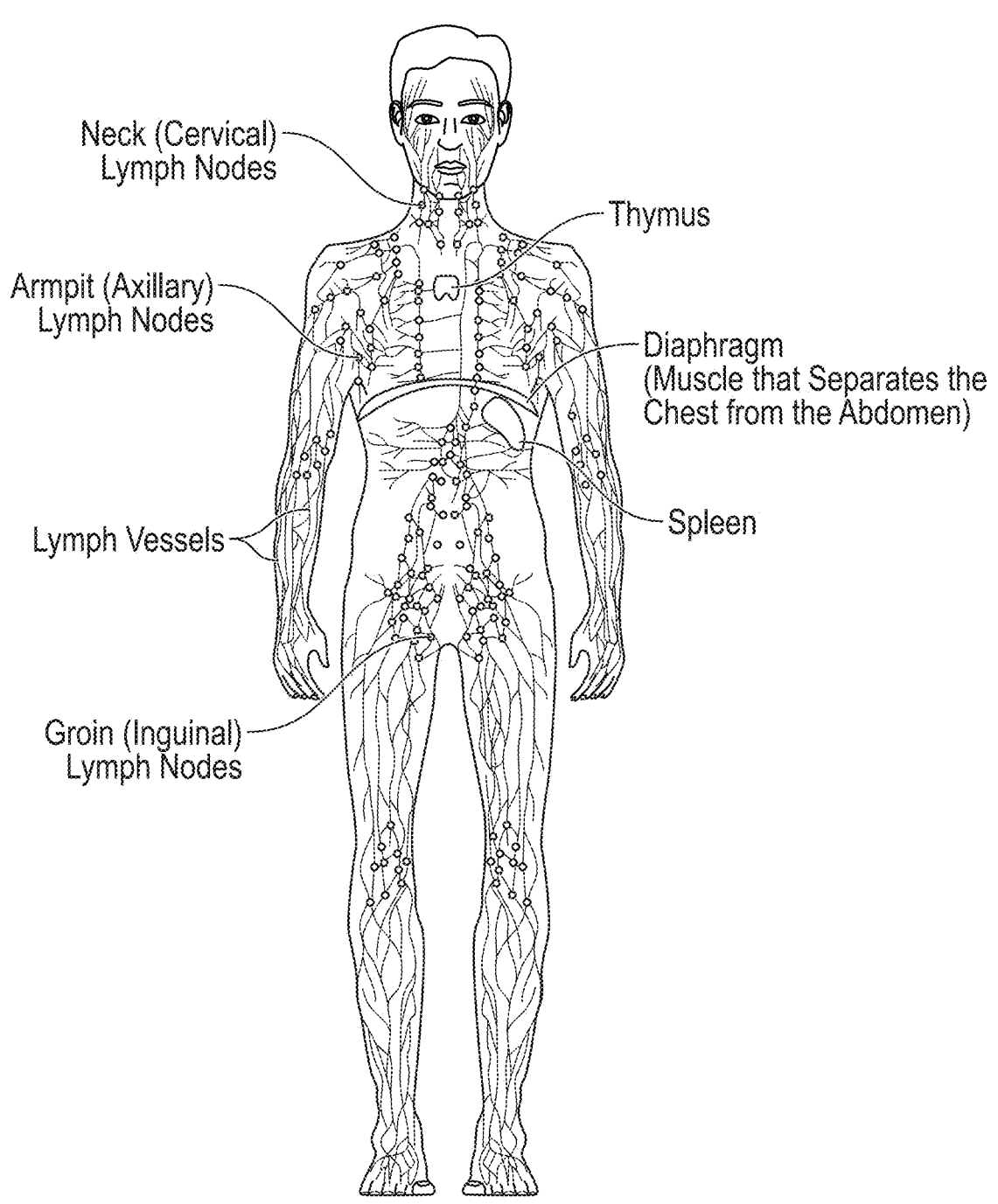
FIG. 1 illustrates the lymphatic system of the human body.

FIG. 1 illustrates a lymphatic system of a body of a user. The lymphatic system is an organ system, which may be a separate and complete body system with its own functional contributions to the human body. The lymphatic system includes a network of lymphatic vessels or channels and nodes, among other features, that help to recirculate blood and/or lymph through the body. As described herein, lymphedema is a medical condition in which excess fluid, such as lymph fluid, collects in an area of the body, such as a limb, and causes swelling (i.e., edema), hardening of the skin, discoloration (e.g., reddening) of the skin, and/or warming of the skin. Left untreated, numerous additional detrimental symptoms may develop.

Figure 2:
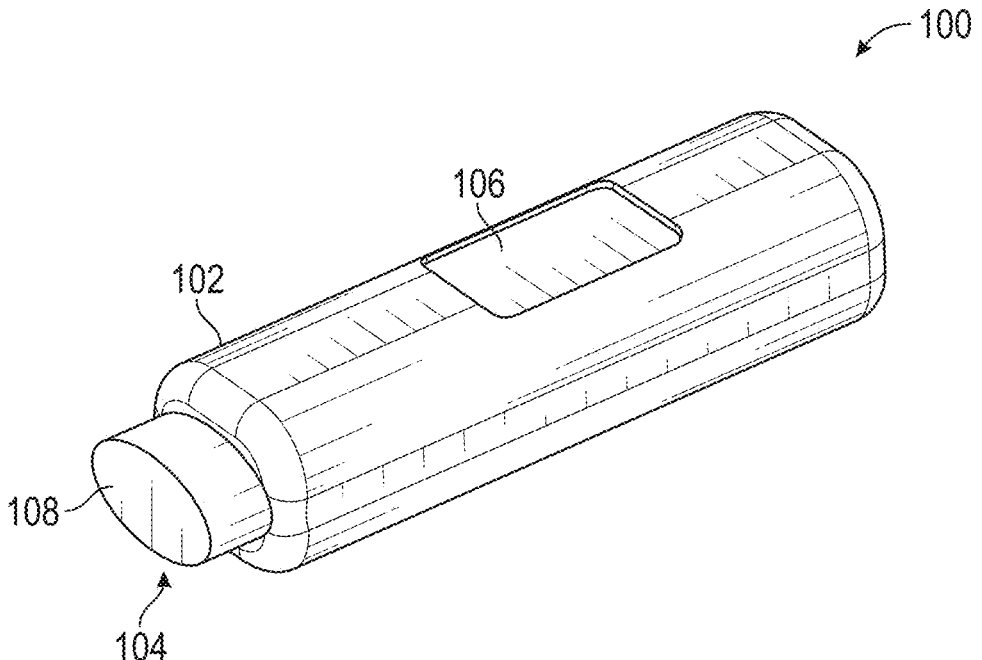
FIG. 2 illustrates a diagnostic device.

FIG. 2 illustrates a diagnostic device 100. The diagnostic device 100 can be used to diagnose, monitor, and/or predict medical conditions, such as lymphedema, edema, circulatory insufficiency, tissue health, ulceration, cellulitis, fibrosis, venous insufficiencies, and/or others. The diagnostic device 100 can be a handheld device or, in some variants, a tabletop device. The diagnostic device 100 can be used by a patient and/or caretaker, enabling the diagnostic device 100 to be used on the go and/or at a home, hospital, clinic, etc. The diagnostic device 100 can communicate with a computing device, such as a portable electronic device (e.g., smart phone), tablet, laptop, desktop, remote computing environment, server, storage device, etc. In some variants, the diagnostic and/or use data generated from the diagnostic device 100 may be relayed to a remote device for review and/or analysis by a caretaker associated with the patient and/or system.

The diagnostic device 100 can include a housing 102 that can house various components of the diagnostic device 100. The housing 102 can be grasped by a user for handling of the diagnostic device 100. The housing 102 can be various sizes and/or shapes. For example, the housing 102 can be an elongate prism with rounded edges, which can improve user comfort.

The diagnostic device 100 can include a head 104, which can also be referred to as a head assembly, tip, and/or end. The head 104 can extend from an end of the housing 102.

The diagnostic device 100 can include one or more sensor(s) 108, e.g., a sensor array, to measure one or more parameters. The one or more sensor(s) 108 can be disposed on the head 104. The one or more sensor(s) 108 can be used to measure one or more parameters of a user, such as temperature (measured at the skin or subcutaneous), percent water content, bioimpedance, hardness or elasticity, oxygen content, tissue dielectric, pulse rate, electromagnetic reflection in the visual and non-visual spectrum, and/or others. Temperature can be measured with at least one or more sensors (measured at the skin or subcutaneous) such as a thermocouple, resistance temperature detector (RTD), thermistor, semiconductor based integrated circuit, and/or infrared thermometer. Percent water content or bioimpedance can be measured with at least one or more sensors using at least multiple-frequency bioimpedance analysis (MFBIA), spectroscopic imaging, derivative spectroscopy visible, infrared, and/or an ultraviolet spectrum, open-ended coaxial probe. Hardness or elasticity can be measured with at least one or more sensors such as a durometer, single or multiple force transducer, strain transducer, pressure transducer, and/or suction with an optical movement sensor. Oxygen content can be measured with at least one or more sensors using at least spectroscopic imaging and/or derivative spectroscopy visible, infrared, and/or ultraviolet spectrum. Pulse rate can be measured with at least one or more sensors using at least spectroscopic imaging, derivative spectroscopy visible, infrared, and ultraviolet spectrum, and/or near-field coherent sensing. Electromagnetic reflection in the visual and non-visual spectrum (picture) can be measured at least with a digital camera sensor and/or photodiode. The one or more sensor(s) 108 can measure one or more of the parameters simultaneously or in succession, which can be at approximately the same point or points on the user (e.g., human or animal). In some variants, the diagnostic device 100 can automatically take one or more measurements when the one or more sensor(s) 108 and/or head 104 is pressed against skin and/or take one or more measurements based on user input via the user interface(s) discussed herein. The measurements can be taken anywhere on the user. In some variants, the measurements can be tracked over time. In some variants, the measurements can be associated with a map to enable the user to track the measurements of the same area over a period of time, which can assist in monitoring progression or regression.

The measurement data for the one or more parameters and/or tissue score described herein can be used to diagnose, monitor, and/or predict medical conditions. The diagnostic device 100 and/or a computing device (portable electronic device (e.g., smart phone), tablet, laptop, desktop, remote computing environment, server, storage device, etc.) in communication (wirelessly or wired) with the diagnostic device 100 can generate a tissue score based on the measurement data for the one or more parameters. The diagnostic device 100 and/or a computing device in communication (wirelessly or wired) with the diagnostic device 100 can clean or filter the measured data. An algorithm can use the measured data for the one or more parameters as the input to generate a tissue score. In some variants, the measured data for the one or more parameters can have equal or unequal weights. For example, for some medical conditions, one or more parameters can be weighted more than another parameter to better diagnose, monitor, and/or predict a condition. The input of multiple parameters can give a more complete picture of the health of the skin and/or underlying tissue. In some variants, the tissue score can be generated based on a comparison with a healthy limb or area of the body. The measurements for the one or more parameters and/or tissue score can be stored on the diagnostic device 100 and/or computing device in communication with the diagnostic device 100. The measurements for the one or more parameters and/or tissue score can be used to guide a treatment regimen.

The diagnostic device 100 can include a user interface 106. The user interface 106 can receive user input and/or display information to the user. The user interface 106 can include one or more toggles, buttons, switches, etc. to receive user input, which can include turning the diagnostic device 100 on or off, commanding the diagnostic device 100 to take one or more measurements, maneuvering through information (e.g., past measurements and/or tissue scores) and/or pages displayed on a display, altering one or more settings, etc. The display can display measurement data and/or tissue scores (past and/or current), settings, messages, instructions (e.g., prompting the user to take a measurement on a specific area of a human or animal), graphics, etc. In some variations, the computing device and/or display in communication with the diagnostic device 100 can display measurement data and/or tissue scores (past and/or current), settings, messages, instructions (e.g., prompting the user to take a measurement on a specific area of a human or animal), graphics, etc.

Figure 3:
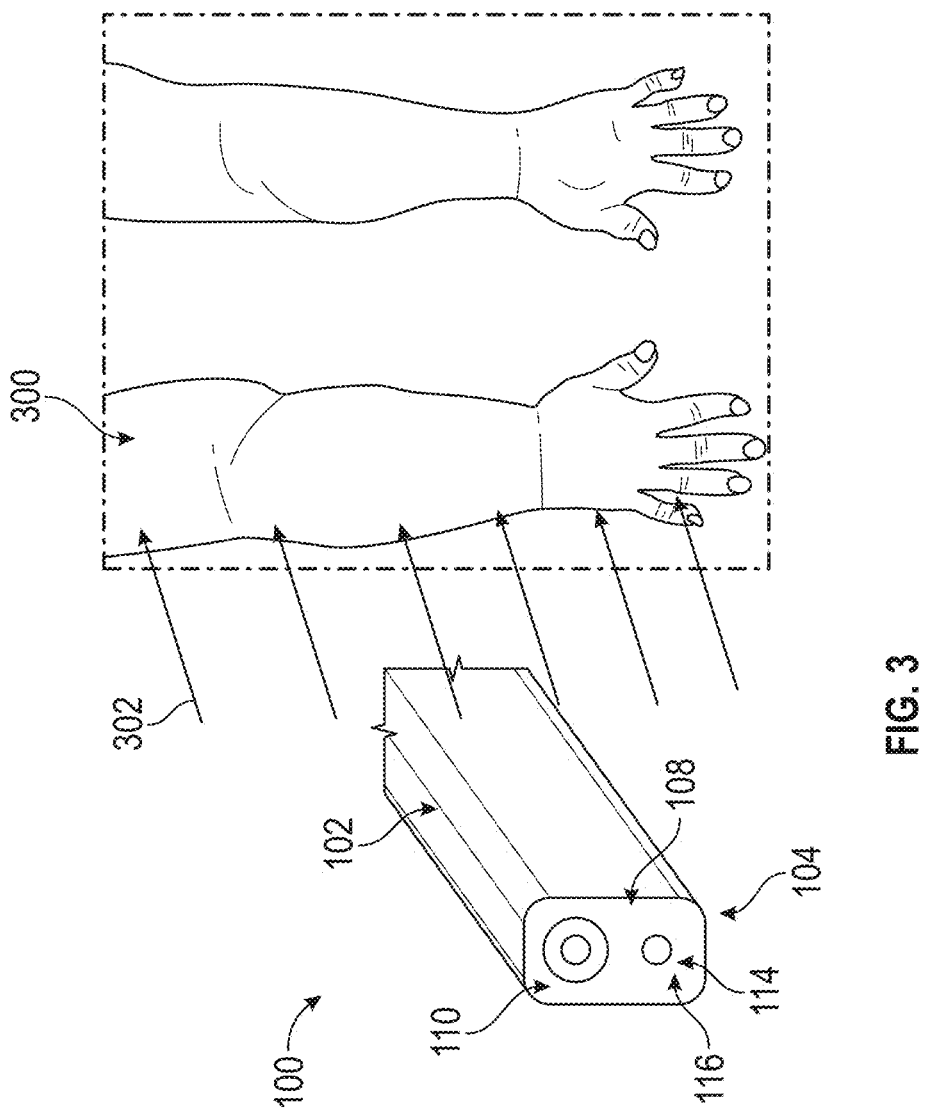
FIG. 3 illustrates a diagnostic device and several testing locations on an arm of a user.
Figures 6A, 6B, 6C, 6D:
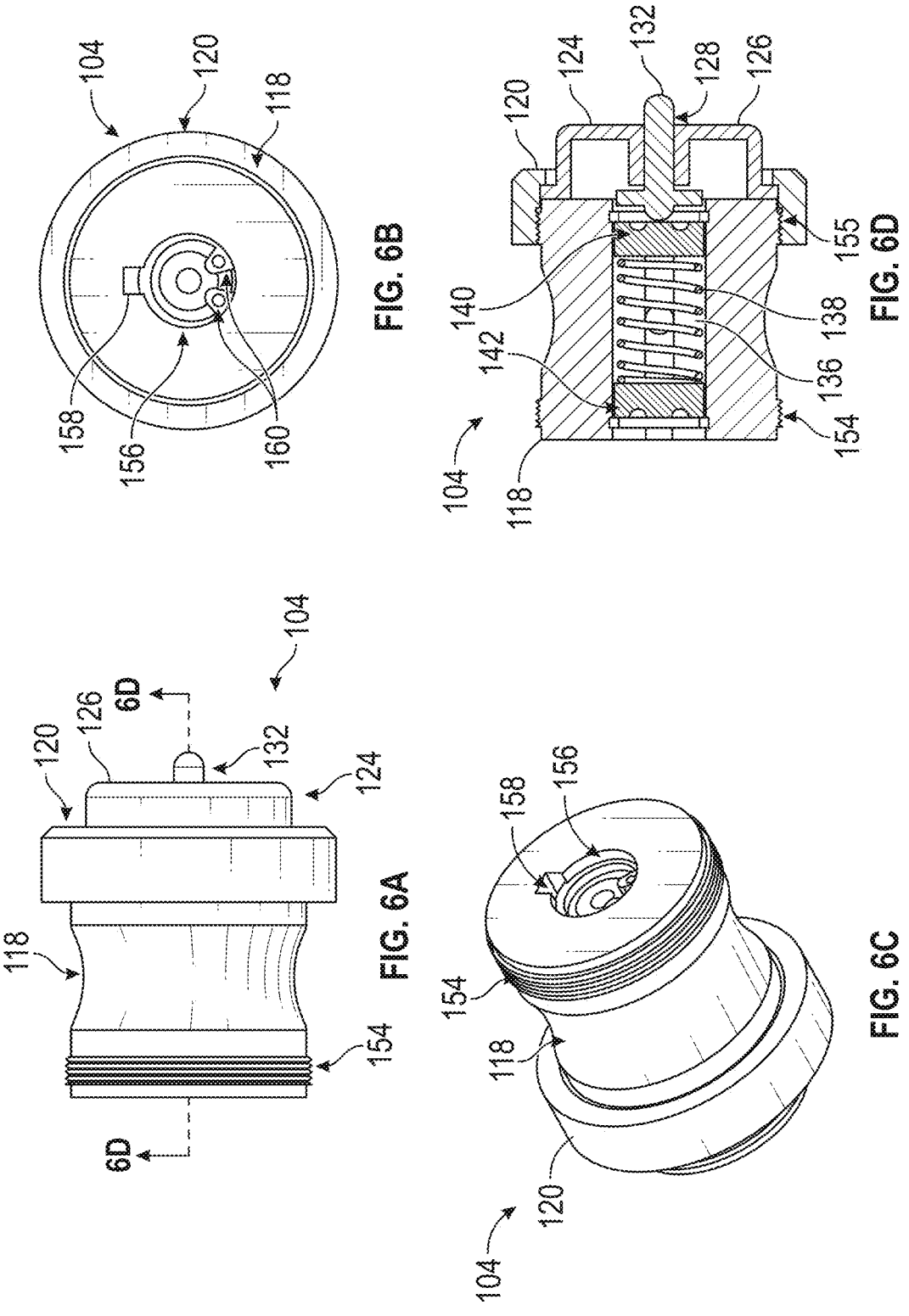
FIG. 6A illustrates a side view of a head assembly.
FIG. 6B illustrates a view if a connection portion of the head assembly of FIG. 6A.
FIG. 6C illustrates a perspective view of the head assembly of FIG. 6A.
FIG. 6D illustrates a section view of the head assembly of FIG. 6A.

FIG. 3 illustrates the diagnostic device 100 and various testing locations 302 on an arm 300 of a user. The diagnostic device 100, as described herein, can include a housing 102, head 104, and/or sensor(s) 108 to measure one or more parameters. The sensor(s) 108 include at least a bioimpedance sensor 110 to measure water content, durometer sensor 116 to measure hardness and/or elasticity, and temperature sensor 114 to measure temperature. The foregoing parameters can be used to diagnose, monitor, and/or predict the course of a medical condition such as lymphedema and/or others. The diagnostic device 100 can be handled by a patient and/or clinician to take one or more measurements, such as the water content, hardness and/or elasticity, and/or temperature, at various testing locations 302 on a user's body, such as the user's arm 300 as illustrated. The measurement data can be cleaned or filtered by the diagnostic device 100 and/or another computing device in communication with the diagnostic device 100. The measurement data can be input into an algorithm that produces a tissue health score for a specific testing location 302, as described herein, such that each testing location 302 has measurement data and/or a tissue health score associated with the testing location 302. The measurement data and/or tissue health score can be tracked over time such that the status of the tissue (e.g., skin) at a testing location 302 can be monitored for diagnosis, treatment, etc.

FIG. 4 illustrates an example head assembly 104, which can also be referred to as a head, tip, and/or end. The head 104 can include the sensors described herein. The head 104 can include a main body 118. The head 104 can include a first retainer 120 and/or second retainer 122 which can be used to retain features on the head 104. The first retainer 120 and second retainer 122 can be rings with openings therethrough with internal threads configured to thread onto the main body 118. For example, the head 104 can have a threaded portion 154 on one side thereof and a threaded portion 155 on an opposite side thereof. The first retainer 120 can engage with the threaded portion 154 to couple to the main body 118 and retain one or more features such as a nose 124 and/or probe 132 and related components to the main body 118. The nose 124 can extend through the opening of the first retainer 120 while being retained to the main body 118. The second retainer 122 can engage with the threaded portion 155 to couple to the main body 118 and retain one or more features to the main body 118.

As described herein, the head 104 can include a durometer. The durometer can include a force transducer. For example, the main body 118 can include a cavity 136. The cavity 136 can house a spring 138 therein. The spring 138 can be disposed between a force transducer body 142 and force transducer tip 140 to transfer forces to facilitate measuring hardness or elasticity. For example, a probe 132, which can also be referred to as a pin or signal probe, can extend through an opening 128 of the nose 124 to contact skin of the user. The probe 132 can be pushed against the skin, exerting a force on the force transducer tip 140 which transfers force to the force transducer body 142 by way of the spring 138 to measure hardness or elasticity. The probe 132 can translate within the opening 128.

The nose 124 can include a contact surface 126. The contact surface 126 can contact the skin of the user as the probe 132 is pressed against the skin to measure hardness or elasticity. In some variants, the nose 124 can include a ground ring 130, which can be disposed on the contact surface 126 and contact the skin of the user while taking a measurement. In some variants, the head 104 can include a temperature sensor 134, which can be disposed on the contact surface 126 such that a temperature measurement can be taken as the contact surface 126 is pressed against the skin. In some variants, the probe 132 and/or other feature of the head 104 or nose 124 can measure bioimpedance/water content percentage of the user. In use, the temperature, hardness or elasticity, and/or bioimpedance can be taken simultaneously as the probe 132 and contact surface 126 are pressed against the skin. In some variants, the temperature, hardness or elasticity, and/or bioimpedance can be taken in succession and/or subgroups (e.g., temperature and bioimpedance together, etc.).

FIGS. 5A and 5B illustrate various views of a nose 124 of the head 104. As described herein, a ground ring 130 can be disposed in the contact surface 126 of the nose 124. The nose 124 can include an opening 128 through which a probe 132 can extend. The ground ring 130 can surround the opening 128 and probe 132. The diagnostic device 100 can include a coaxial cable 146. A wire can connect the coaxial cable 146 to the ground ring 130. A wire can connect the coaxial cable 146 to the washer 152, which in some embodiments is simply a contact configured to form an electrical connection between the coaxial cable 146 and the pressure sensor 148. In use, the probe 132 can push against the skin to exert a force on the pressure sensor 148 with the washer 152 disposed therebetween to measure hardness or elasticity. The diagnostic device 100 can include a ring 144 disposed around the probe 132. The ring 144 can be disposed on the inside of the nose 124.

As described herein, the nose 124 can include a temperature sensor 134, which can be disposed in the contact surface 126 such that the temperature sensor 134 contacts the skin of the user as the probe 132 and contact surface 126 contact the skin. The diagnostic device 100 can include a printed circuit board 150, which can be operatively connected to the temperature sensor 134 and/or other features. The printed circuit board 150 can be a flexible printed circuit board.

FIGS. 6A-6D illustrate various views of the head 104. The head 104 can include the sensors described herein. As described herein, the head 104 can include a main body 118. The head 104 can include a first retainer 120 to retain one or more features to the main body 118. The main body 118 can include the threaded portion 154 and threaded portion 155. The first retainer 120 can be threaded onto the main body 118 on the threaded portion 155 to retain the nose 124 and the probe 132. As described herein, the head 104 can include a durometer, which can include a force transducer. For example, the main body 118 can include a cavity 136. The cavity 136 can house a spring 138 therein. The spring 138 can be disposed between a force transducer body 142 and force transducer tip 140 to transfer forces to facilitate measuring hardness or elasticity. The head 104 can include an opening 156, which can be positioned on a side of the head 104 opposite the probe 132. The opening 156 can include a notch 158. The head 104 can include a stop 160, which can extend into the opening 156, and which may be configured to stop or limit the travel of the probe 132. For example, the stop 160 may limit the amount of force that may be applied to the transducer.

Figure 7:
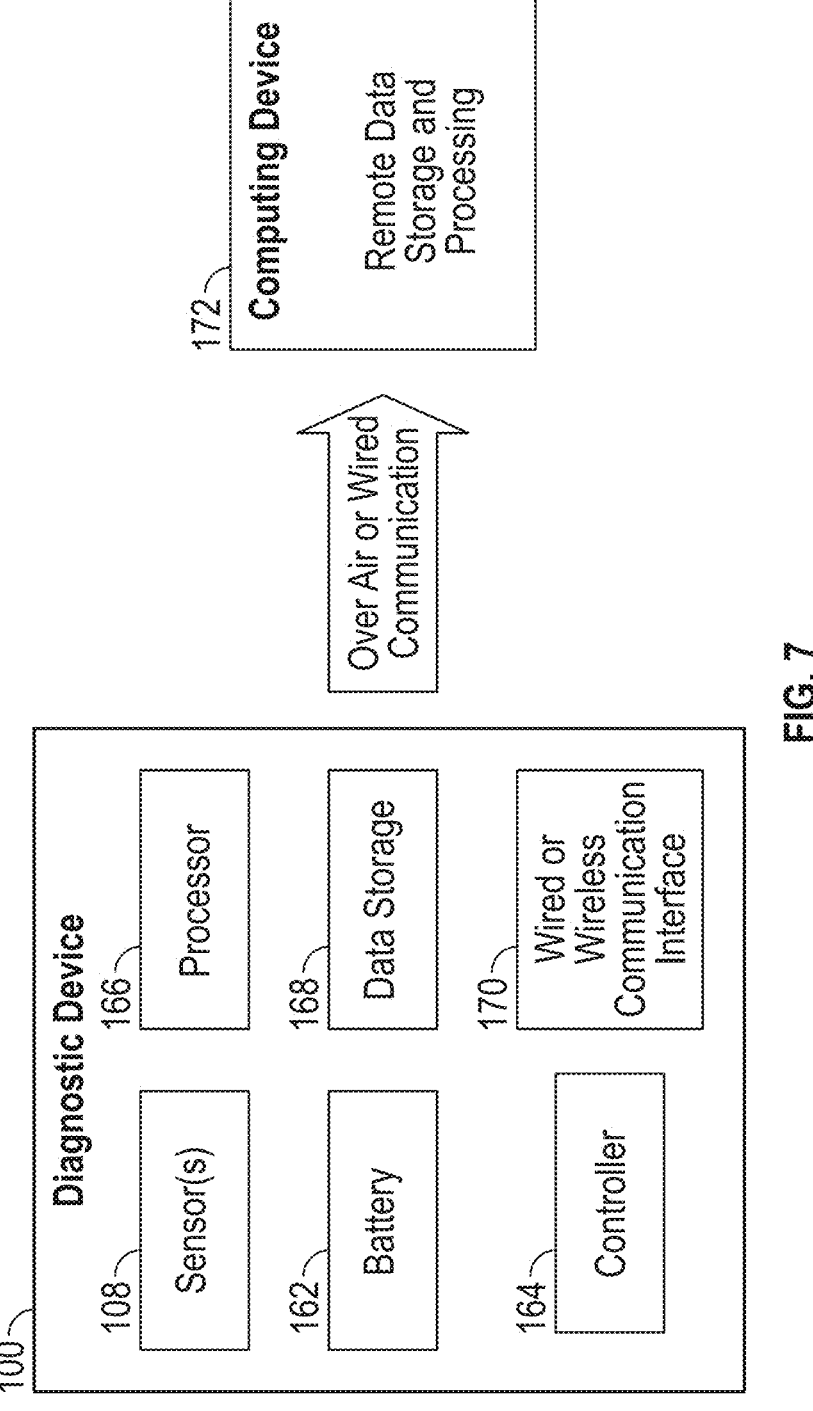
FIG. 7 illustrates a schematic of a diagnostic device and a computing device.

FIG. 7 illustrates a schematic diagnostic device 100 and a computing device 172, which can include a computer, tablet, smart phone, remote computing environment, etc. The diagnostic device 100 can include a sensor(s) 108, battery 162, controller 164, processor 166, data storage 168, wired or wireless communication interface 170, and/or any other features to perform the functions described herein. As described herein, the diagnostic device 100 can take the measurements and/or calculate the health tissue score. The diagnostic device 100 can communicate (e.g., wired, WI-FI, Bluetooth, cellular networks such as 3G, 4G, and 5G, etc.), by way of the wired or wireless communication interface 170, with the computing device 172. In some variants, the diagnostic device 100 can take measurements and relay the measurement data to the computing device 172 for processing, storage, and/or generating the tissue health score. In some variants, the diagnostic device 100 can take measurements, process the measurement data, generate the tissue health score, store data, etc. and relay the measurement data, tissue health score, etc. to the computing device 172 for storage, further processing, and/or display on a display of the computing device 172. For example, in some variants, the computing device 172 can have a display through which the user and/or a caretaker can review and/or analyze measurement data, health tissue score, record messages, etc. The computing device 172 can be at least a portable electronic device (e.g., smart phone), tablet, laptop, desktop, remote computing environment, server, storage device, etc.

Figure 8:
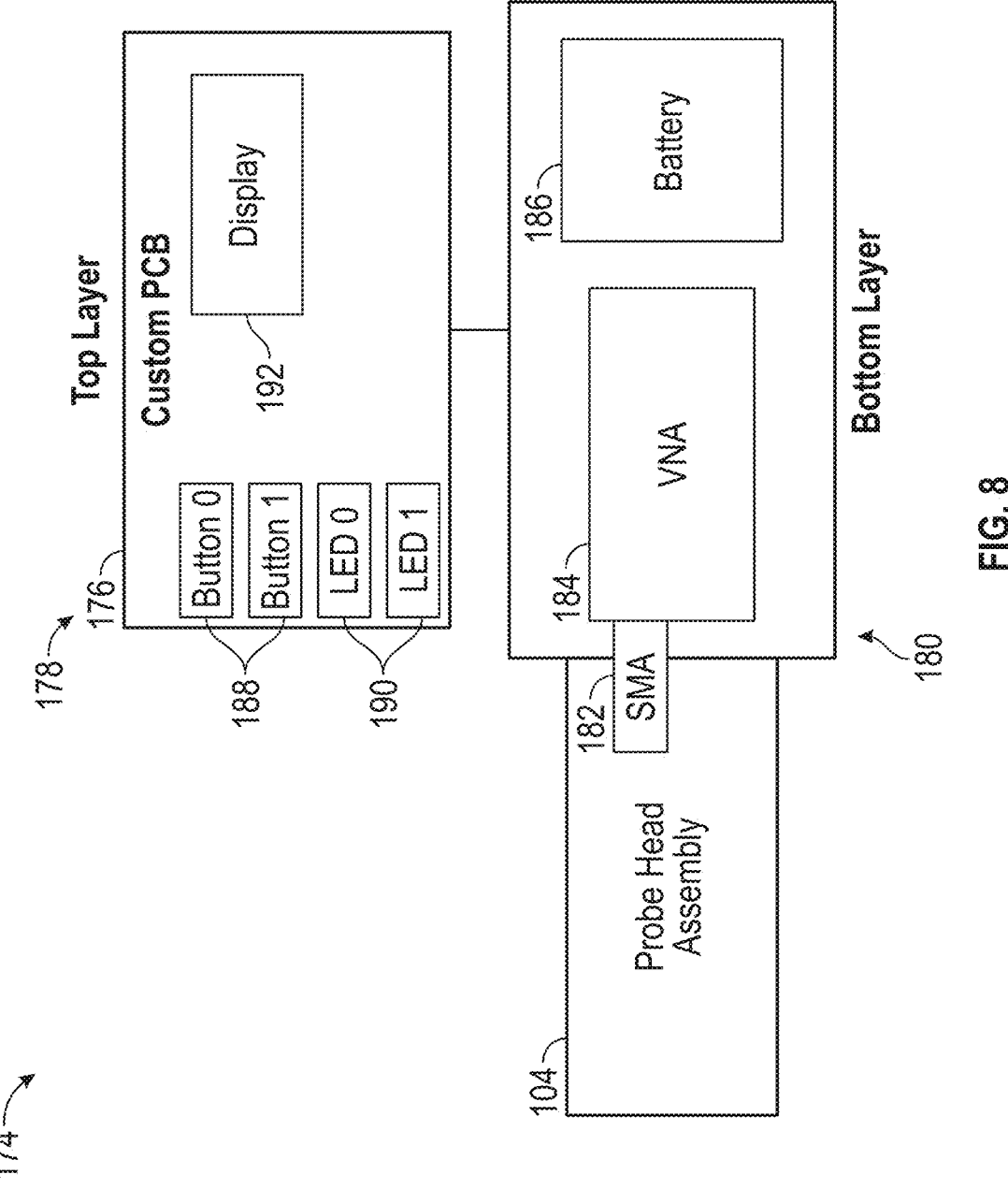
FIG. 8 illustrates a schematic of a handheld diagnostic device.

FIG. 8 illustrates a schematic of a handheld diagnostic device 174. The diagnostic device 174 can include any of the features of the diagnostic device 100 or other diagnostic device described herein. The diagnostic device 174 can include a printed circuit board 176 that can include a display 192, one or more buttons 188, one or more LEDs 190, and/or other features, which can be incorporated into a to a top layer 178. The display 192 can communicate instructions, measurement data for one or more parameters, a tissue health score, and/or other information to the user. In some variants, the display 192 can be a touchscreen. The top layer 178 can be in communication with one or more features of a bottom layer 180. The diagnostic device 174 can include a head 104, which can also be referred to as a probe head assembly, that is in communication with a vector network analyzer 184 by way of a connector 182. The head 104 can include any of the sensors described herein and be configured to contact the skin of the patient. The diagnostic device 174 can be powered by a battery 186, which can be disposable or rechargeable. The head 104, connector 182, vector network analyzer 184, and/or battery 186 can be incorporated into a bottom layer 180 of the diagnostic device 174.

Figure 9:
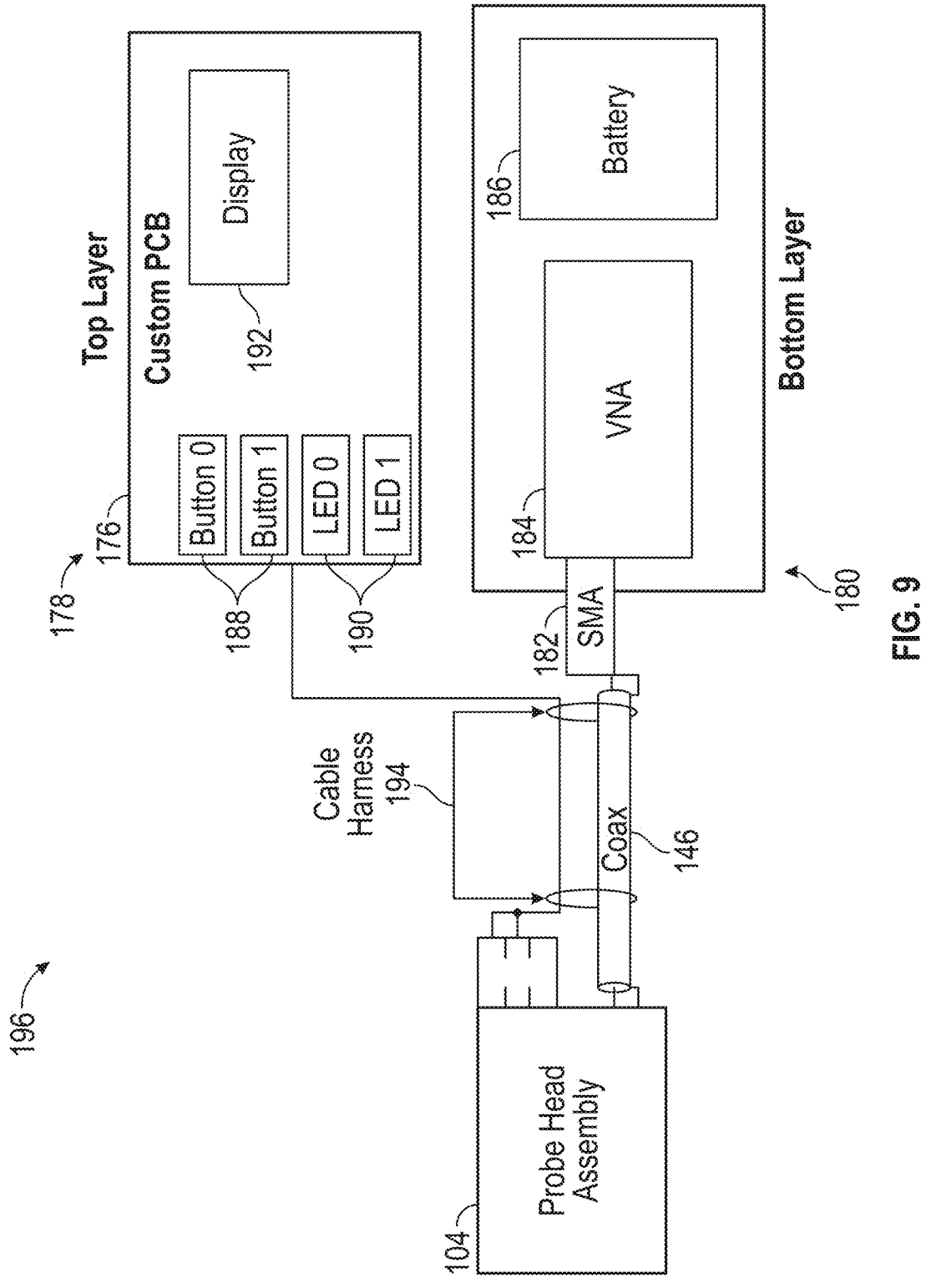
FIG. 9 illustrates a schematic of a tabletop diagnostic device.

FIG. 9 illustrates a schematic of a table top diagnostic device 196. The diagnostic device 196 can include any of the features of the diagnostic device 100 or other diagnostic device described herein. The table top diagnostic device 196 can include a printed circuit board 176 that can include a display 192, one or more buttons 188, one or more LEDs 190, and/or other features, which can be incorporated into a top layer 178. The table top diagnostic device 196 can include a connector 182 operatively connected to a vector network analyzer 184, which can be incorporated into a bottom layer 180. The table top diagnostic device 196 can include a battery 186 and/or power connection for power, which can be incorporated into the bottom layer 180. The table top diagnostic device 196 can include a head 104, which can also be referred to as a probe head assembly. The head 104 can include any of the sensors described herein and be configured to contact the skin of the patient. The head 104 can be operatively connected to the top layer 178 and bottom layer 180, which can be by way of a coaxial cable 146. For example, a coaxial cable 146 can connect the head 104 and the bottom layer 180 by way of the connector 182. A wired connection, which can be a coaxial cable, can connect the head 104 to the top layer 178. The one or more wired connections from the head 104 to the top layer 178 and bottom layer 180 can be bound together by a cable harness 194.

Figure 10:
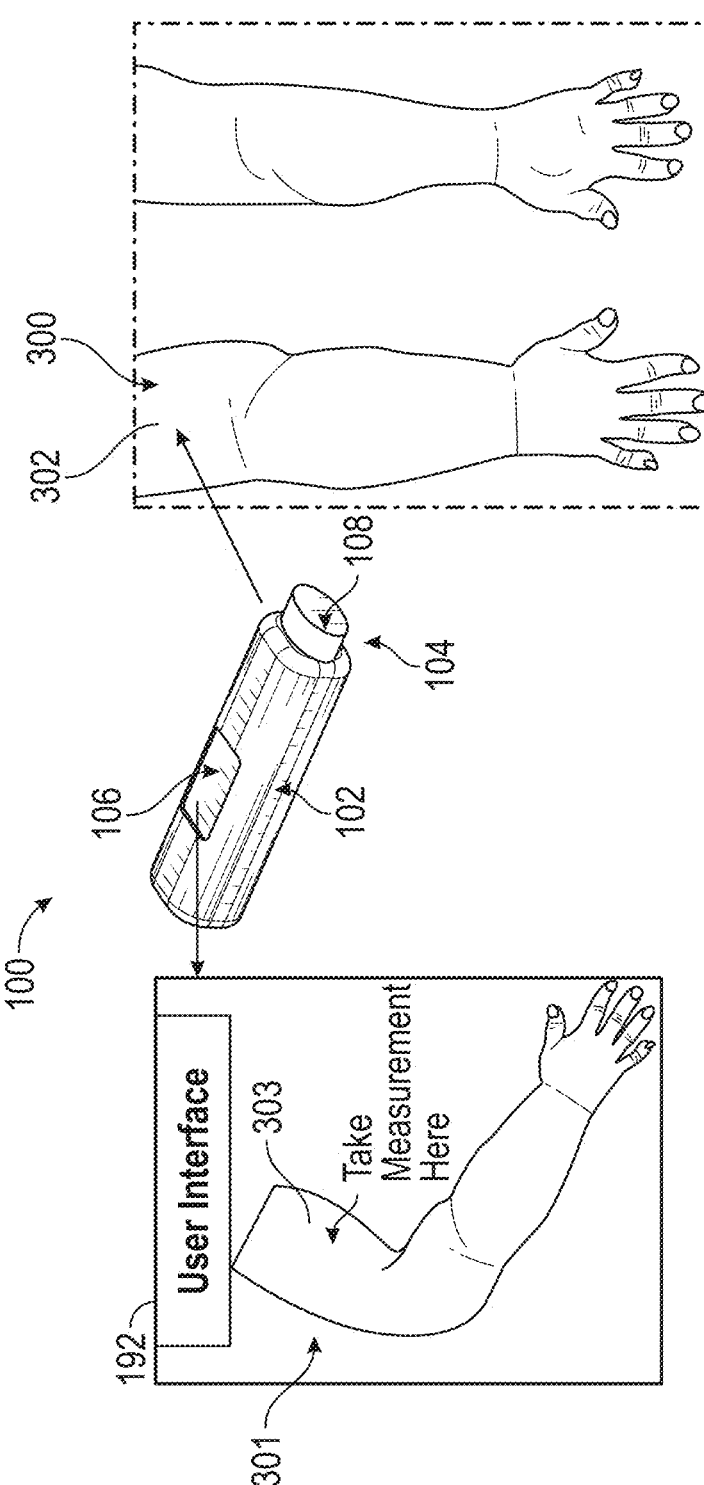
FIG. 10 illustrates a display of a diagnostic device indicating a testing location on the arm of the user.

FIG. 10 illustrates a display 192 of a diagnostic device 100. The diagnostic device 100 can include a user interface 106 which can include the display 192. The display 192 can provide instructions to the user, such as where to take a measurement. For example, the display 192 can depict a representation of a portion of the user's body, such as representation arm 301, and indicate a representation testing location 303 on the representation arm 301 at which a measurement should be taken. The user can, based on the instruction, contact the sensor(s) 108 on the head 104 of the diagnostic device 100 with the skin of the user at the testing location 302 on the user's arm 300 that corresponds to the representation testing location 303 on the representation arm 301 displayed on the user interface 106. This can help the user to take one or more measurements for one or more parameters at a specific location, which can help to facilitate tracking one or more parameters and/or a tissue health score at a specific location over time. In some variants, the diagnostic device 100 can communicate with a remote device. The remote device can include a display which can provide instructions to the user to take one or more measurements at a specific location on the user's body, as described herein. The diagnostic device 100 and/or remote device can instruct the user to take one or more measurements at any location on a body. In some variants, measurements can be taken on a body and associated with a map of the body to track the same area over time (e.g., multiple measurements). For example, in some variants, the user may take a measurement at a testing location 302 on the arm 300 and the diagnostic device 100 and/or associated remote device may record the testing location 302 and associated data and/or associate the testing location 302 and/or data with a map of the user's body to track the same area over multiple measurements.

Figure 11:
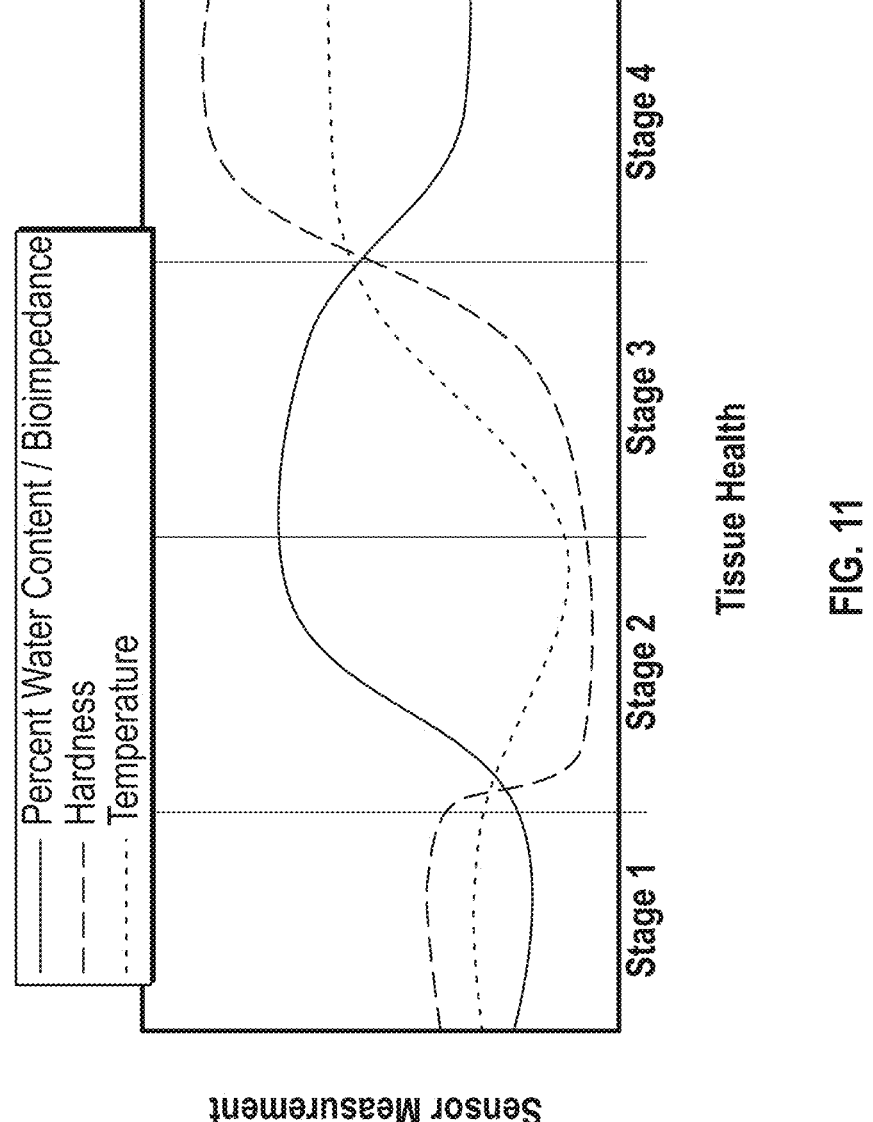
FIG. 11 illustrates various sensor measurements (percent water content/bioimpedance, hardness, and temperature) over stages of tissue health for lymphedema.

As described herein, the one or more measurements for one or more parameters can be used to create a tissue health score for the user. The use of multiple parameters to generate a tissue health score can give a more complete picture of the health of the skin and/or underlying tissue of a patient. FIG. 11 illustrates a graph showing sensor measurements for three parameters at four stages of tissue health (e.g., tissue health scores) of a patient suffering from lymphedema. The three parameters graphed are percent water content/bioimpedance, hardness, and temperature. The stages can progress in severity from stage one, which can correspond with an initial stage of lymphedema, to stage four, which can correspond with an advanced stage of lymphedema with more severe symptoms. The measurements for the three parameters can vary at the four stages of lymphedema, which can help to generate a tissue health score (e.g., stage of development) that is a more complete picture of the health of the skin and/or underlying tissue.

Measurements for the three parameters can be taken by a diagnostic device. The measurement data for the three parameters can be used to determine if the patient's lymphedema is at stage one, two, three, or four to provide a quantifiable metric for diagnosis, treatment, and/or monitoring. In some variants, less than three or more than three parameters can be measured to generate a tissue health score. In some variants, other parameters can be used to generate a tissue health score. In some variants, the measurements are compared with data associated with healthy or unhealthy skin to generate a tissue health score. In some variants, the measurements are input into an algorithm, which may compare the measurement data with data associated with healthy or unhealthy skin, to generate a tissue health score.

Figure 12:
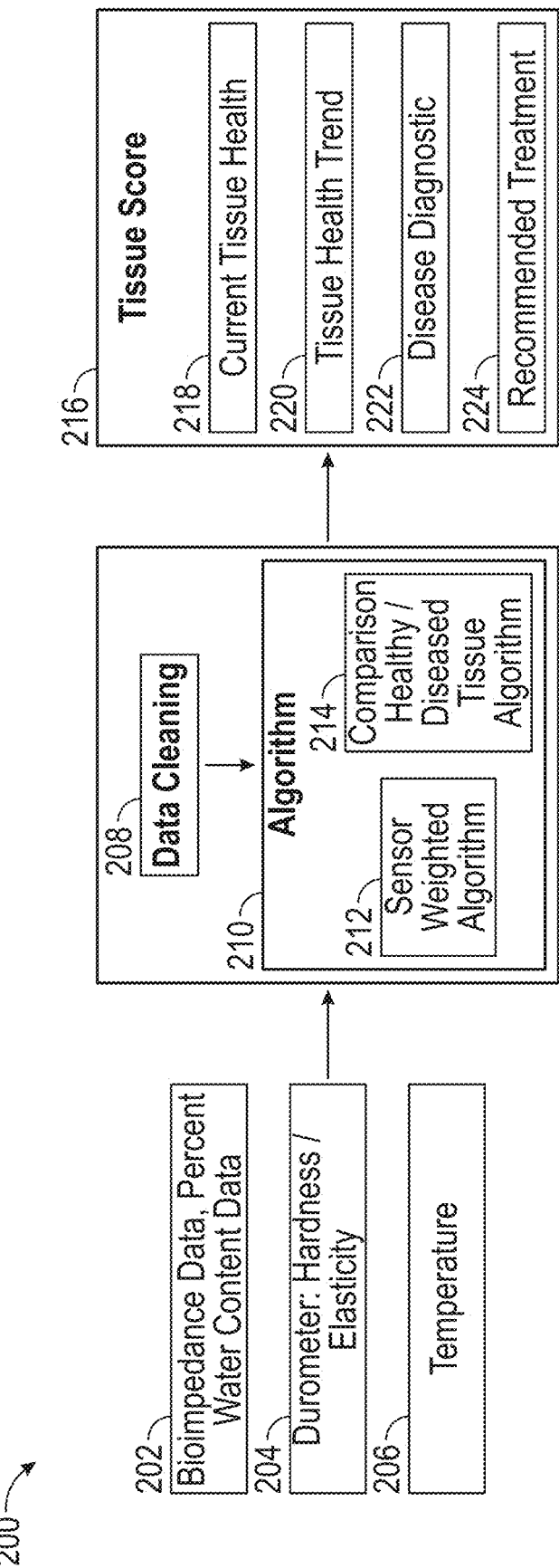
FIG. 12 illustrates a process for producing a tissue health score and other information based on tissue health score and/or sensor measurements.

FIG. 12 illustrates a process for producing a tissue health score and other information based on tissue health score and/or sensor measurements. As described herein, the process can being by using the diagnostic device can be used to obtain measurement data relating to one or more parameters for a patient. For example, the diagnostic device by way of one or more sensors may be pressed against and/or proximate the skin of a user to obtain measurement data, such as bioimpedance data 202, hardness data 204, and/or temperature data 206 for the user at a location on the user's body. In some variants, measurement data for other parameters can be obtained for the user. The process can advance to data cleaning step 208. The measurement data can be cleaned (e.g., filtered) using one or more techniques. In some variants, the measurement data is not cleaned. The process can advance to the algorithm step 210 and the cleaned measurement data can be input into one or more algorithms to generate a tissue score 216 and/or other information. For example, in some variants, the cleaned measurement data can be input into a sensor weighted algorithm 212, which can weigh one or more parameters heavier than one or more other parameters, to generate a tissue score 216 and/or other information. In some variants, the cleaned measurement data can be input to a comparison algorithm 214 that can compare the cleaned measurement data with data associated with healthy or diseased skin or tissue to generate a tissue score 216 and/or other information. In some variants, the combined weighted measurement data or weighted delta of measurement values between healthy tissue and/or skin and diseased tissue and/or skin can be used as the variables of a predictive algorithm to generate a tissue score. The measurement data, foregoing delta, and/or tissue score can be tracked over time. The algorithm can have variable weights depending on the stage of disease.

As described herein, the algorithm can generate a tissue score 216 which can provide a quantifiable metric that provides a more complete indication of skin or tissue health. In some variants, the algorithm and/or associate feature can output an indication and/or description of current tissue health 218, tissue health trend 220, disease diagnostic 222, and/or recommended treatment 224, which can be displayed to the user at least by way of the techniques described herein. The tissue health trend 220 can be based on measurement data and/or tissue health scores over a period of time.

Figure 13:
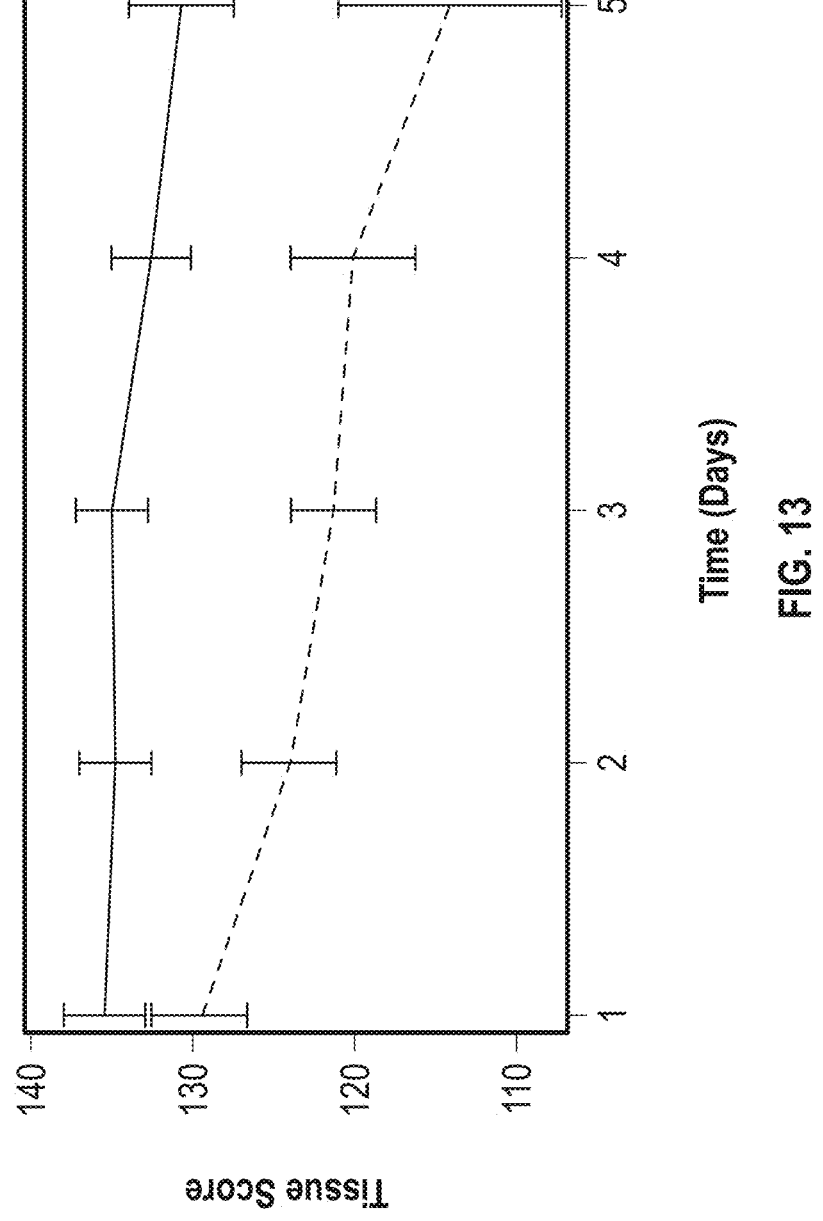
FIG. 13 illustrates a graph of generated tissue scores over time.
Figure 14:
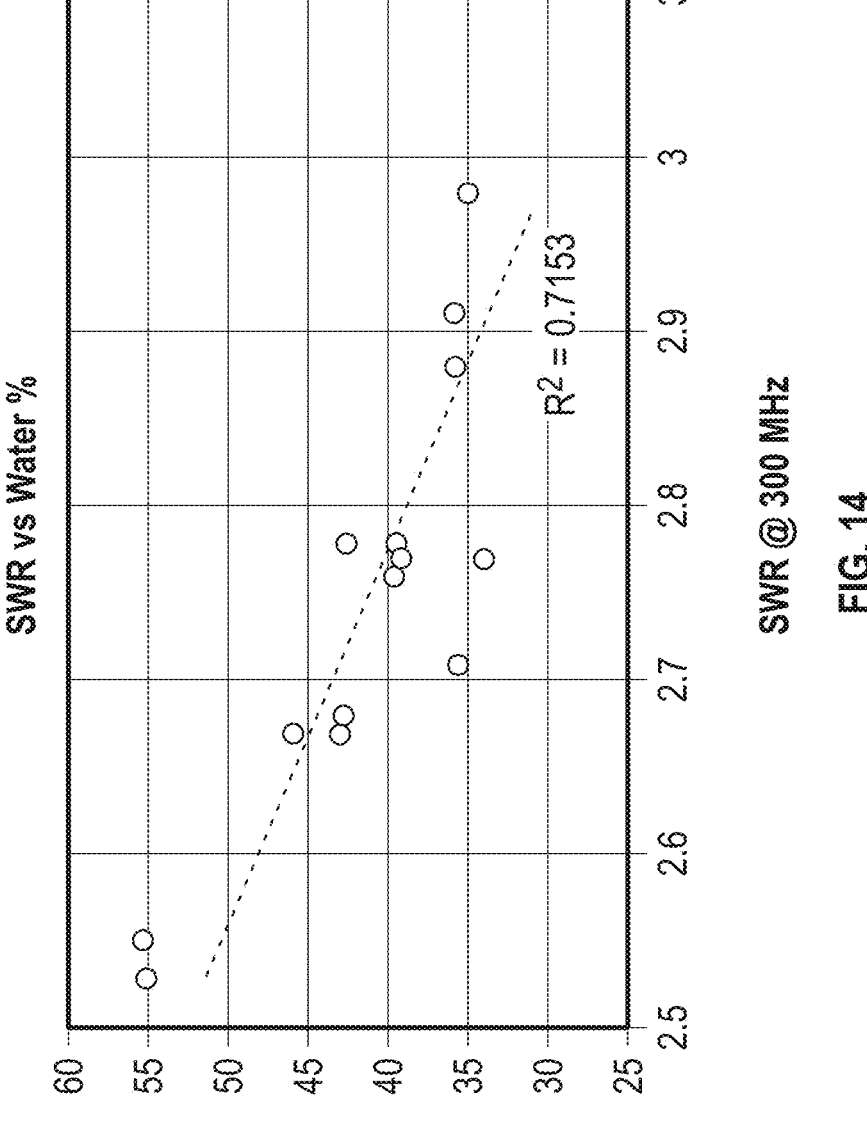
FIG. 14 illustrates a graph of water percent content against standing wave ratio measurements.
Figure 15:
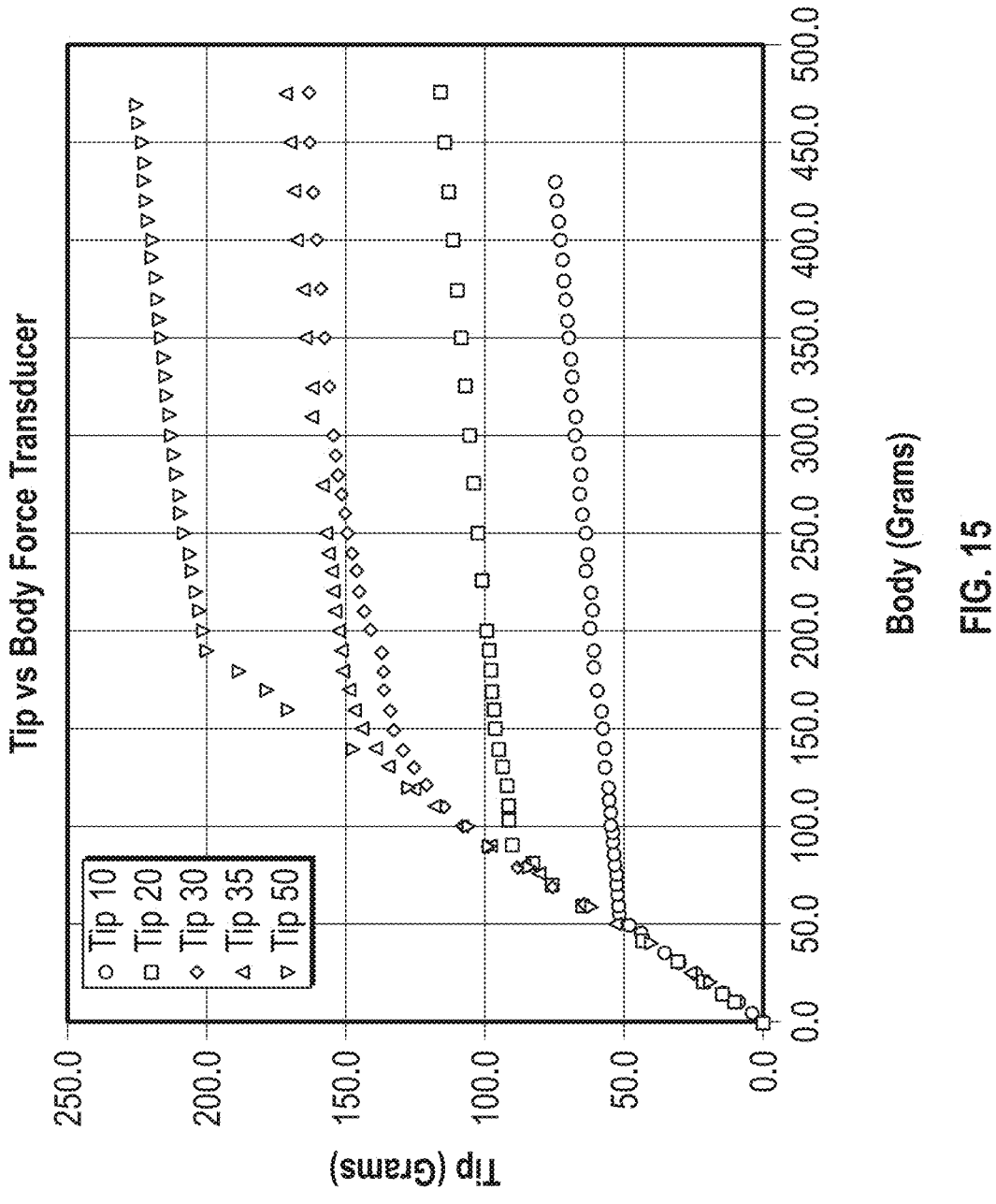
FIG. 15 illustrates a graph of tip against body force transducer.

FIG. 13 illustrates a graph of generated tissue scores over time. As described herein, the tissue health scores over time can be used to determine a tissue health trend, which can be useful for treatment. FIG. 14 a graph of water percent content against standing wave ratio measurements. FIG. 15 illustrates a graph of tip against body force transducer.

FIGS. 16A and 16B illustrate a head 304, which may be a head assembly, tip, and/or end portion, for a diagnostic device 100. The head 304 may be disposed on an end portion of the diagnostic device 100. The head 304 may at least include any of the features, including one or more sensors, described in reference to any of the other heads and/or diagnostic devices described herein. The head 304 may include one or more features to measure the bioimpedance/ percent water content of tissue. For example, the head 304 may include a dielectric probe 331 (e.g., dielectric conductor) and ground ring 330 to take dielectric measurements to measure bioimpedance/water content percentage of tissue. The dielectric probe 331 maybe coaxially positioned relative to the ground ring 330. The dielectric probe 331 may be centered within the ground ring 330. A contact surface 326, which may be an insert, may be positioned between the dielectric probe 331 and the ground ring 330. The contact surface 326 may be an insulator, such as polytetrafluoroethylene (PTFE) (e.g., TEFLON™), to electrically insulate the dielectric probe 331 from the ground ring 330. The contact surface 326 may be part of a ring shaped insulator. In some embodiments, the dielectric probe 331, contact surface 326, and ground ring 330 may be pressed against tissue to take dielectric measurements to measure bioimpedance/water content percentage of tissue. As illustrated in FIG. 16B, the dielectric probe 331, contact surface 326, and ground ring 330 may be flush. In some variants, the dielectric probe 331, contact surface 326, and ground ring 330 may not be flush. The ground ring 330 may be a continuous ring. In some variants, the ground ring 330 may not be continuous. In some variants, the ground ring 330 may be not be annular in shape but others, which may at least include polygonal (e.g., square, rectangle, etc.) irregular, and/or others.

The head 304 may include a durometer 333 (e.g., durometer sensor, durometer probe) to measure the hardness and/or elasticity of tissue. The durometer sensor 333 may be disposed outside of (e.g., radially outward relative to) the ground ring 330. In some variants, the durometer sensor 333 may be disposed inside of (e.g., radially inward relative to) the ground ring 330. The head 304 may include a temperature sensor 134 to measure the temperature of tissue (measured at the skin and/or subcutaneous). The temperature sensor 134 may be disposed outside of (e.g., radially outward relative to) to the ground ring 330. In some variants, the temperature sensor 134 may be disposed inside of (e.g., radially inward relative to) the ground ring 330.

FIGS. 17A and 17B illustrate a head 404, which may be a head assembly, tip, and/or end portion, for a diagnostic device 100. The head 404 may be disposed on an end portion of the diagnostic device 100. The head 404 may at least include any of the features, including one or more sensors, described in reference to any of the other heads and/or diagnostic devices described herein. The head 404 may include one or more features to measure the percent water content of tissue. For example, the head 404 may include a probe 432, which may be the same as or similar to the probe 132. The probe 432 can be at least dual purpose and be used to measure the hardness and/or elasticity of tissue and/or to take dielectric measurements to measure bioimpedance/ water content percentage of tissue. The head 404 may include a ground ring 430. The probe 432 may be coaxially positioned relative to the ground ring 430. The probe 432 may be centered within the ground ring 330. A contact surface 426, which may be an insert, may be positioned between the probe 432 and the ground ring 430. The contact surface 426 may be an insulator, such as polytetrafluoroethylene (PTFE) (e.g., TEFLON™), to electrically insulate the probe 432 from the ground ring 430. The contact surface 426 may be part of a ring-shaped insulator. In some embodiments, the probe 432, contact surface 426, and/or ground ring 430 may be pressed against tissue to take hardness and/or elasticity measurements and/or dielectric measurements to measure bioimpedance/water content percentage of tissue. As illustrated in FIG. 17B, the probe 432 may extend away from the ground ring 430 and/or contact surface 426.

The head 404 may include a temperature sensor 134 to measure the temperature of tissue (measured at the skin and/or subcutaneous). The temperature sensor 134 may be disposed inside of (e.g., radially inward relative to) the ground ring 430. The temperature sensor 134 may be disposed at least partially within and/or on the contact surface 426. In some variants, the temperature sensor 134 may be disposed outside of (e.g., radially outward relative to) to the ground ring 430.

Figures 18A, 18B, 18C, 19A, 19B, 20A, 20B:
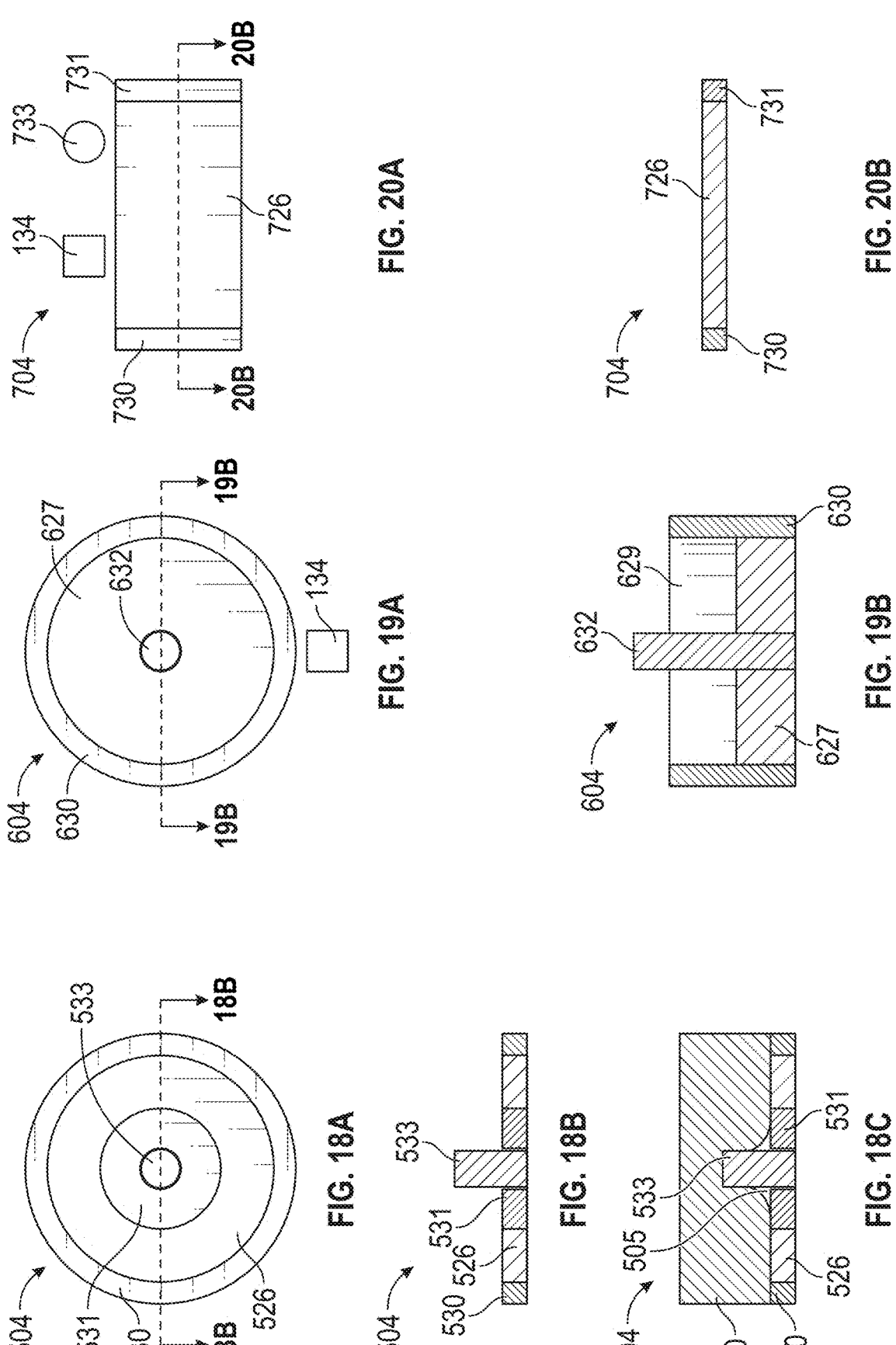
FIG. 18A illustrates another head assembly for a diagnostic device.
FIG. 18B illustrates a side cross-section view of the head assembly of FIG. 18A.
FIG. 18C illustrates the side cross-section view of the head assembly of FIG. 18B contacting tissue.
FIG. 19A illustrates another head assembly for a diagnostic device.
FIG. 19B illustrates a side cross-section view of the head assembly of FIG. 19A.
FIG. 20A illustrates another head assembly for a diagnostic device.
FIG. 20B illustrates a side cross-section of the head assembly of FIG. 20A.

FIGS. 18A and 18B illustrate a head 504, which may be a head assembly, tip, and/or end portion, for a diagnostic device 100. The head 504 may be disposed on an end portion of the diagnostic device 100. The head 504 may at least include any of the features, including one or more sensors, described in reference to any of the other heads and/or diagnostic devices described herein. The head 504 may include one or more features to measure the percent water content of tissue. For example, the head 504 may include a dielectric probe 531 (e.g., dielectric conductor) and ground ring 530 to take dielectric measurements to measure bioimpedance/water content percentage of tissue. The dielectric probe 531 may be a ring structure. The dielectric probe 531 may be coaxially positioned relative to the ground ring 530. The dielectric probe 531 may be centered within the ground ring 530. A contact surface 526, which may be an insert, may be positioned between the dielectric probe 531 and the ground ring 530. The contact surface 526 may be part of an insulator, such as polytetrafluoroethylene (PTFE) (e.g., TEFLON™), to electrically insulate the dielectric probe 531 from the ground ring 530. The contact surface 526 may be part of a ring shaped insulator. In some embodiments, the dielectric probe 531, contact surface 526, and/or ground ring 530 may be pressed against tissue to take dielectric measurements to measure bioimpedance/water content percentage of tissue.

The head 504 may include a durometer sensor 533 (e.g., durometer, durometer probe) that may measure the hardness and/or elasticity of tissue. The durometer sensor 533 may be positioned inward (e.g., radially inward) relative to the dielectric probe 531 and ground ring 530. As illustrated in FIG. 18B, the durometer sensor 533 may extend away from the ground ring 530, contact surface 526, and/or dielectric probe 531. The ground ring 530, contact surface 526, and/or dielectric probe 531 may be flush relative to each other, as shown in FIG. 18B. The head 504 may include a temperature sensor to measure the temperature of tissue (measured at the skin and/or subcutaneous). In some variants, the dielectric probe 531 may be biased outward by a spring but may be pushed against tissue to be flush with the dielectric probe 531, contact surface 526, and/or ground ring 530.

As shown in FIG. 18C, when the head 504 is pressed against tissue 550, a gap 505 (e.g., air gap) may be disposed between the tissue 550 and a portion of the dielectric probe 531. The gap 505 may present challenges when taking dielectric measurements.

FIGS. 19A and 19B illustrate a head 604, which may be a head assembly, tip, and/or end portion, for a diagnostic device 100. The head 604 may be disposed on an end portion of the diagnostic device 100. The head 604 may at least include any of the features, including one or more sensors, described in reference to any of the other heads and/or diagnostic devices described herein. The head 604 may include one or more features to measure the percent water content of tissue. For example, the head 604 may include a probe 632, which may be the same as or similar to the probe 132. The probe 632 can be at least dual purpose and be used to measure the hardness and/or elasticity of tissue and/or to take dielectric measurements to measure bioimpedance/water content percentage of tissue. The head 604 may include a ground ring 630. The probe 632 may be coaxially positioned relative to the ground ring 630. The probe 632 may be centered within the ground ring 630. An insulator 627, which may be an insert, may be positioned between the probe 632 and the ground ring 630. The insulator 627 (e.g., polytetrafluoroethylene (PTFE), such as TEFLON™) may electrically insulate the probe 632 from the ground ring 630. The insulator 627 may be ring shaped. In some embodiments, the probe 632 and ground ring 430 may be pressed against tissue to take hardness and/or elasticity measurements and/or dielectric measurements to measure bioimpedance/water content percentage of tissue.

As illustrated in FIG. 19B, the probe 632 may extend away from a leading edge of the ground ring 630 and/or insulator 627. A gap 629, which may be an annular gap, may be disposed between the probe 632 and ground ring 630. The insulator 627 may be recessed relative to a leading edge of the ground ring 630 and end portion of the probe 632 such that the gap 629 is disposed inward relative to the leading edge of the ground ring 630. When processing dielectric measurements, the gap 629 can be accounted for and the dielectric measurements may be shifted accordingly, which can help alleviate issues caused by the gap 505 described in reference to FIG. 18C.

The head 604 may include a temperature sensor 134 to measure the temperature of tissue (measured at the skin and/or subcutaneous). The temperature sensor 134 may be disposed outside of (e.g., radially outward relative to) to the ground ring 630. In some variants, the temperature sensor 134 may be disposed inside of (e.g., radially inward relative to) the ground ring 630.

FIGS. 20A and 20B illustrate a head 704, which may be a head assembly, tip, and/or end portion, for a diagnostic device 100. The head 704 may be disposed on an end portion of the diagnostic device 100. The head 704 may at least include any of the features, including one or more sensors, described in reference to any of the other heads and/or diagnostic devices described herein. The head 704 may include one or more features to measure the percent water content of tissue. For example, the head 704 may include a dielectric probe 731 (e.g., dielectric conductor) and ground conductor 730 to take dielectric measurements to measure bioimpedance/water content percentage of tissue when pressed against the tissue. The dielectric conductor 731 may have a periphery with different shapes, which may at least include polygonal (e.g., square, rectangle, etc.), circular, oval, etc. The ground conductor 730 may have a periphery with different shapes, which may at least include polygonal (e.g., square, rectangle, etc.), circular, oval, etc. The dielectric conductor 731 and ground conductor 730 may be the same or similar in shape and/or size. The dielectric conductor 731 and ground conductor 730 may be offset from each other. The dielectric conductor 731 and ground conductor 730 may be parallel relative to each other. The head 704 may include a contact surface 726 that may be disposed between the dielectric conductor 731 and ground conductor 730. The contact surface 726 may be part of an electrical insulator, such as those described herein. The contact surface 726 may have a periphery that has different shapes, which can at least include polygonal (e.g., square, rectangle, etc.). The ground conductor 730, dielectric conductor 731, and contact surface 726 may be pressed against tissue to take dielectric measurements. The ground conductor 730, dielectric conductor 731, and contact surface 726 may be flush relative to each other as shown in FIG. 20B.

The head 704 may include a durometer sensor 733 (e.g., durometer probe) that may used to measure the hardness and/or elasticity of tissue. The head 704 may include a temperature sensor 134 to measure the temperature of tissue (measured at the skin and/or subcutaneous). The durometer sensor 733 and/or temperature sensor 134 may be disposed at a position not between the ground conductor 730 and dielectric conductor 731. In some variants, the durometer sensor 733 and/or temperature sensor 134 may be disposed between the ground conductor 730 and dielectric conductor 731.

Figures 21A, 21B:
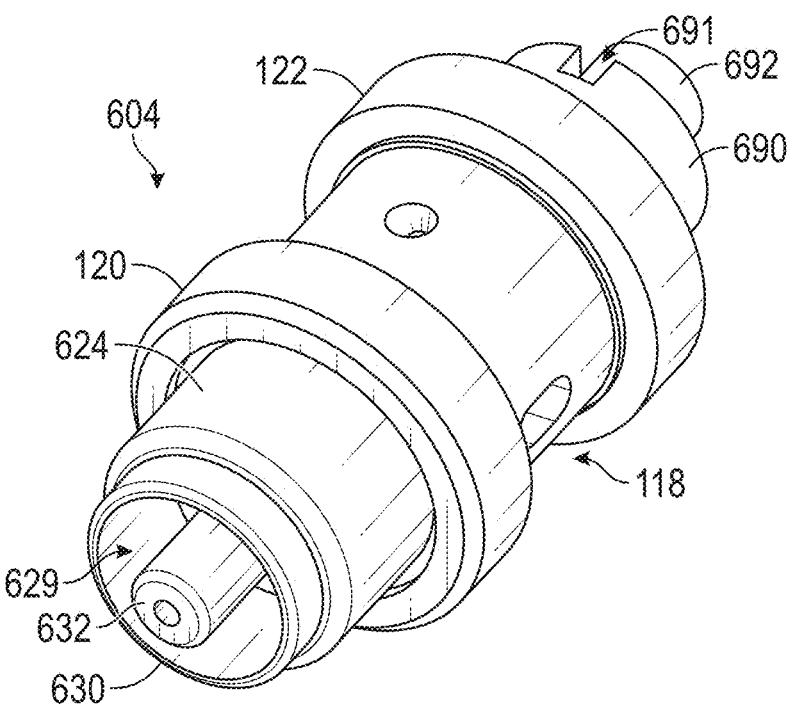
FIG. 21A illustrates a perspective view of the head assembly of FIG. 19A.
FIG. 21B illustrates a side cross-section of the head assembly of FIG. 21A.

FIGS. 21A and 21B illustrate view of the head 604. As shown in FIG. 21A, the head 604 can include a main body 118. The ground ring 630, insulator 627, and probe 632 can be coupled to the main body 118. For example, the head 604 can include a housing 624 (e.g., annular structure) that can be circumferentially disposed around the ground ring 630. The housing 624 can extend along at least a portion of a length of the ground ring 630. The housing 624 can be an annular structure. The housing 624, ground ring 630, insulator 627, and probe 632 can be secured, directly or indirectly, to the main body 118 by a first retainer 120. The head 604 may include a second retainer 122 that may retain an annular structure 690 and/or fixture 692, directly or indirectly, to the main body 118. The annular structure 690 may include a notch 691. The second retainer 122 may be disposed on an opposing side of the main body 118 relative to the first retainer 120. The main body 118 may be a cylindrical structure. The first retainer 120 and/or second retainer 122 may be annular structures. The first retainer 120 and second retainer 122 may be secured to the main body 118 at threaded portions 154, 155, as described herein.

As described herein, the head 604 may include a probe 632 that may at least be a probe for a durometer and/or dielectric sensor. The probe 632 can cooperate with a force transducer to detect hardness and/or elasticity of tissue. For example, as shown in FIG. 21B, the main body 118 may include a cavity 136. The cavity 136 may house a spring 138. The spring 138 may be disposed between a force transducer body 142 and force transducer tip 140 to transfer forces to facilitate measuring hardness and/or elasticity. For example, the probe 632, which can be a pin or signal probe, can be pressed against tissue, exerting a force on the force transducer tip 140 which may transfer force to the force transducer body 142 by way of the spring 138 to measure hardness and/or elasticity. In some variants, the probe 632 may be translated and the spring 138 compressed until the end of the probe 632 is at least flush with the leading edge of the ground ring 630.

The main body 118 may include a plurality of apertures therethrough. The plurality of apertures may include longitudinal apertures 676, 677 that may be oriented parallel relative to a longitudinal axis of the main body 118. The plurality of apertures may include perpendicular apertures 672, 674 that may be oriented perpendicularly relative to the longitudinal axis of the main body 118.

Figures 22A, 22B:
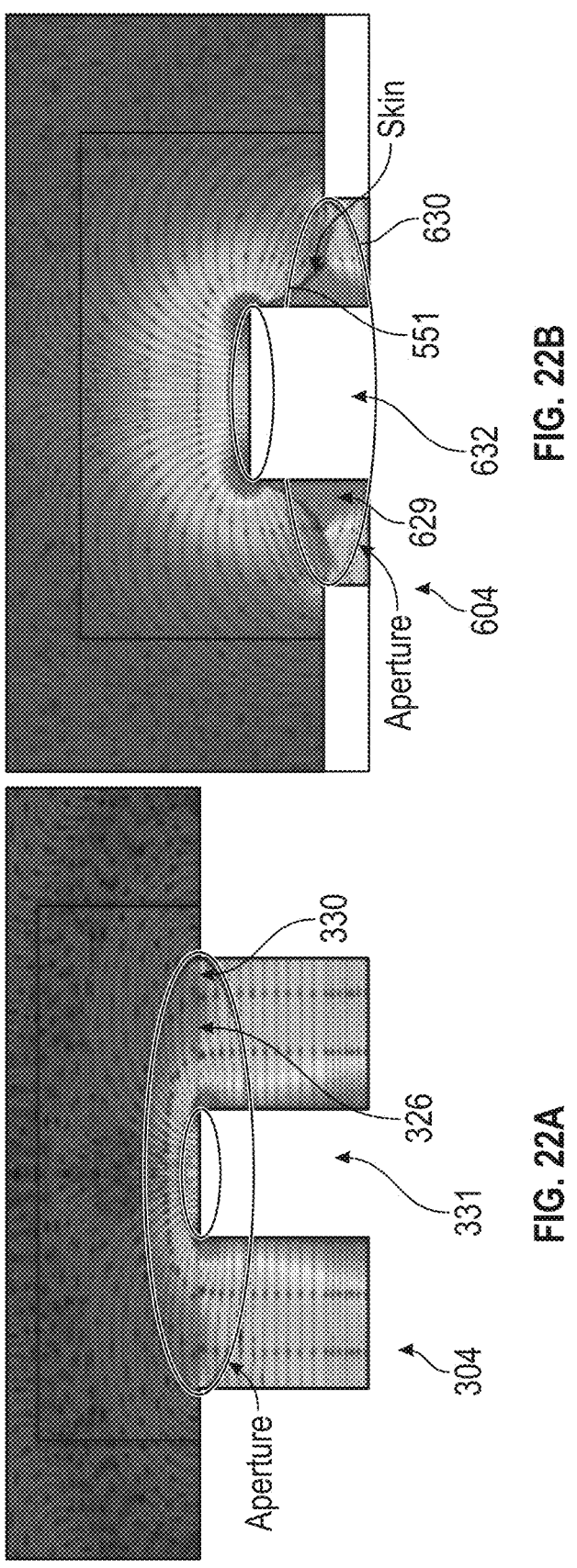
FIG. 22A illustrates a simulated electrical field for a head assembly similar to the head assembly shown in FIG. 16A.
FIG. 22B illustrates a simulated electrical field for a head assembly similar to the head assembly shown in FIG. 19A.

FIG. 22A illustrates a simulated electrical field for a head assembly similar to the head 304 described in reference to FIGS. 16A and 16B when contacting tissue. FIG. 22B illustrates a simulated electrical field for a head assembly similar to the head 604 described in reference to FIGS. 19A, 19B, 21A, and 21B when contacting tissue. As shown, skin 551 extends from a leading edge of the probe 632 to a leading edge of the ground ring 630 over the gap 629.

Figures 23A, 23B:
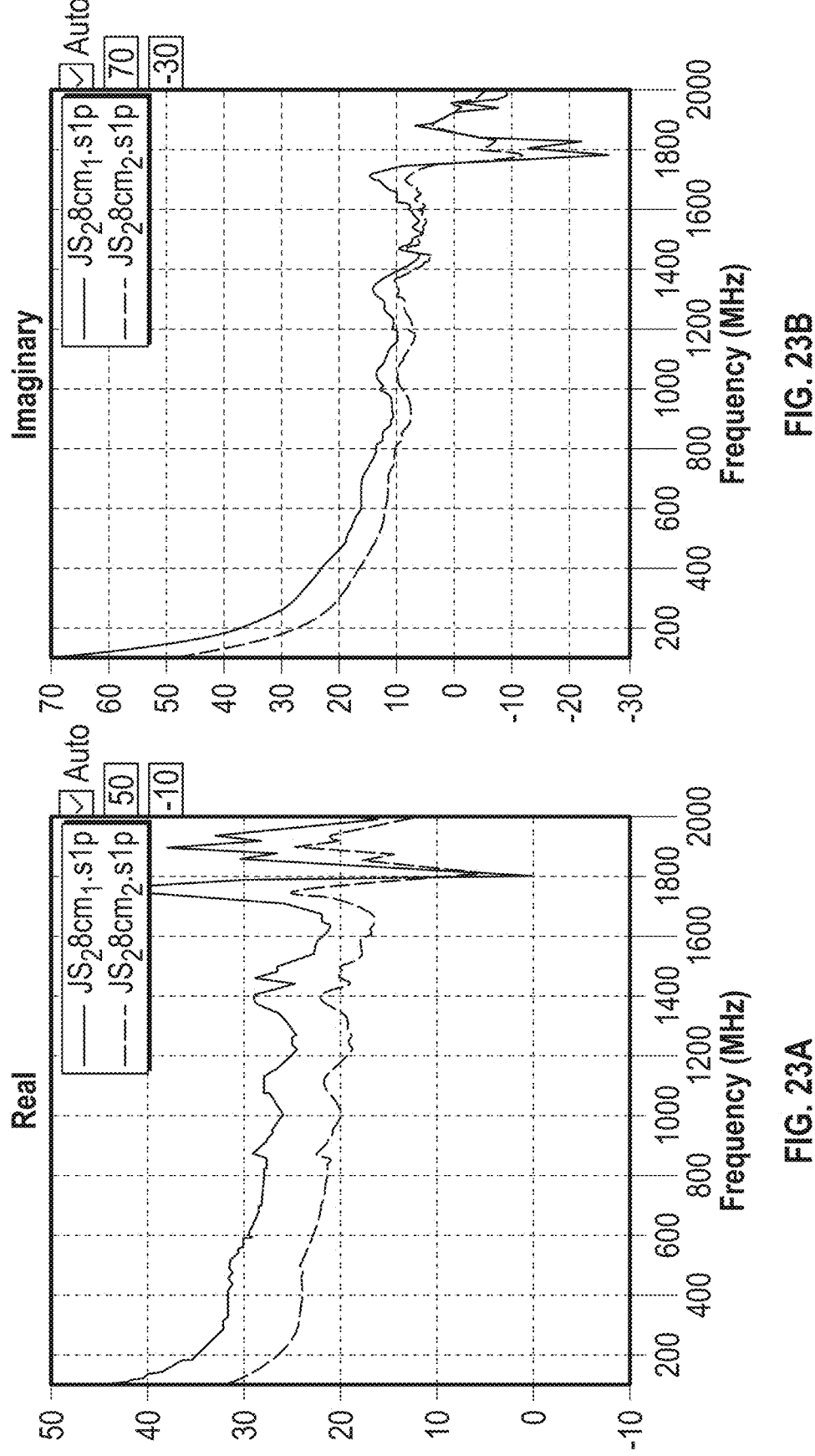
FIG. 23A illustrates a graph of clinical data for the real part of a dielectric measurement.
FIG. 23B illustrates a graph of clinical data for the imaginary part of a dielectric measurement.

FIG. 23A illustrates a graph of clinical data for the real part of a dielectric measurement. FIG. 23B illustrates a graph of clinical data for the imaginary part of a dielectric measurement.

Terminology

Although the systems and methods have been disclosed in the context of certain embodiments and examples, it will be understood by those skilled in the art that the systems and methods extend beyond the specifically disclosed embodiments to other alternative embodiments and/or uses of the embodiments and certain modifications and equivalents thereof. Various features and aspects of the disclosed embodiments can be combined with or substituted for one another in order to form varying modes. The scope of this disclosure should not be limited by the particular disclosed embodiments described herein.

Methods of using the foregoing system(s) (including device(s), apparatus(es), assembly(ies), structure(s) or the like) are included; the methods of use can include using or assembling any one or more of the features disclosed herein to achieve functions and/or features of the system(s) as discussed in this disclosure. Methods of manufacturing the foregoing system(s) are included; the methods of manufacture can include providing, making, connecting, assembling, and/or installing any one or more of the features of the system(s) disclosed herein to achieve functions and/or features of the system(s) as discussed in this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Some embodiments have been described in connection with the accompanying drawings. Components can be added, removed, and/or rearranged. Orientation references such as, for example, "top" and "bottom" are for ease of ease of discussion and may be rearranged such that top features are proximate the bottom and bottom features are proximate the top. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

In summary, various embodiments and examples of diagnostic devices and methods have been disclosed. Although the systems and methods have been disclosed in the context of those embodiments and examples, it will be understood by those skilled in the art that this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

What is claimed is:

1. A diagnostic device for measuring a hardness and a bioimpedance of a tissue, the diagnostic device comprising:
   a bioimpedance sensor, the bioimpedance sensor comprising a conductive probe, wherein the bioimpedance sensor is configured to measure the bioimpedance of the tissue;
   an electrical ground surrounding at least a portion of the conductive probe, wherein the conductive probe is stationary with respect to the diagnostic device; and
   a durometer sensor, the durometer sensor comprising a durometer probe disposed radially inward of the conductive probe and extending past a tip of the conductive probe, the durometer probe moveable with respect to the conductive probe, wherein the durometer sensor is configured to measure the hardness of the tissue.

2. The diagnostic device of claim 1, wherein the bioimpedance and hardness measurements are used to generate a tissue health score for the tissue.

3. The diagnostic device of claim 1, further comprising a temperature sensor configured to measure a temperature of the tissue.

4. The diagnostic device of claim 3, wherein the bioimpedance, hardness, and temperature measurements are used to generate a tissue health score for the tissue.

5. The diagnostic device of claim 1, further comprising an insulator disposed between the conductive probe and the electrical ground.

6. The diagnostic device of claim 5, wherein the insulator is offset from a leading edge of the electrical ground such that an air gap is disposed between the conductive probe and the electrical ground.

7. The diagnostic device of claim 1, further comprising a force transducer body, a force transducer tip, and a spring disposed between the force transducer body and the force transducer tip, and wherein the durometer probe is configured to be pushed by the tissue to translate the force transducer tip toward the force transducer body to measure the hardness of the tissue.

8. The diagnostic device of claim 1, wherein the diagnostic device is configured to measure the hardness of the tissue and the bioimpedance of the tissue simultaneously.

9. The diagnostic device of claim 1, wherein the diagnostic device prompts a user to take measurements at a location on a body of the user.

10. The diagnostic device of claim 1, wherein a computing device in communication with the diagnostic device prompts a user to take measurements at a location on a body of the user.

* * * * *